(12) United States Patent
Browning et al.

(10) Patent No.: US 6,312,691 B1
(45) Date of Patent: Nov. 6, 2001

(54) LYMPHOTOXIN-α/β COMPLEXES AND ANTI-LYMPOTOXIN-β RECEPTOR ANTIBODIES AS ANTI-TUMOR AGENTS

(76) Inventors: Jeffrey L. Browning, 32 Milton Rd., Brookline, MA (US) 02146; Werner Meier, 31 Bedford St., Burlington, MA (US) 01803; Christopher D. Benjamin, 2 Oak Hill La., Beverly, MA (US) 01915

(*) Notice: Subject to any disclaimer, the term of this patent is extended or adjusted under 35 U.S.C. 154(b) by 0 days.

(21) Appl. No.: 08/875,560

(22) PCT Filed: Jan. 26, 1996

(86) PCT No.: PCT/US96/01386

§ 371 Date: Jun. 5, 1998

§ 102(e) Date: Jun. 5, 1998

(87) PCT Pub. No.: WO96/22788

PCT Pub. Date: Aug. 1, 1996

(51) Int. Cl.[7] ................................................. A61K 39/395
(52) U.S. Cl. ......................... 424/143.1; 424/130.1; 424/144.1; 424/809; 530/388.22; 530/388.7; 530/388.75; 530/388.8; 530/388.85
(58) Field of Search .............................. 424/130.1, 143.1, 424/144.1, 809; 530/388.22, 388.7, 388.75, 388.8, 388.85

(56) References Cited

FOREIGN PATENT DOCUMENTS

WO 92/00329    1/1992   (WO).
WO 94/13808    6/1994   (WO).

OTHER PUBLICATIONS

Acharya, S.K., 1993, Indian J. Med. Res., Apr. pp. 69–74, "A Preliminary open trial on interferon stimulator (SNMC) derived from *Glycyrrhiza glabra* in the treatment of subacute hepatic failure".

Aggarwal, Bharat, 1984, J. of Biological Chem., 259:686–691, "Production By A Lymphoblastoid Cell Line, Purification, and Initial Characterization".

Alderson, Mark R., 1994, International Immunology, 6:1799–1806, "Regulation of Apoptosis and T cell activation by Fas-specific mAb".

Androlewicz, Matthew, J. of Biological Chem., 1992, 267:2542–2547, "Lymphotoxin Is Expressed as a Heteromeric Complex with a Distinct 33-kDa Glycoprotein on the surface of an Activated Human T Cell Hybridoma".

Arulanandam, Antonio R., 1993, J. Exp. Med., 177:1439–1450, "A Soluble Multimeric Recombinant CD2 Protein Identifies CD48 as a Low Affinity Ligand for Human CD2: Divergence of CD2 Ligands during the Evolution of Humans and Mice".

Bernstein, David, 1993, Antiviral Research, 20:45–55, "Effects of therapy with an immunomodulator (imiquimod, R-837) along and with acyclovir on genital HSV–2 infection in guinea–pigs when begun after lesion development".

Browning, Jeffrey, Androlewicz, Matthew et al., 1991, J. of Immunology, 147:1230–1237, "Lymphotoxin and an Associated 33–kDa Glycoprotein Are Expressed on the Surface of an Activated Human T Cell Hybridoma".

Browning, Jeffrey and Douglas, Irene et al., 1995, J. of Immunology, 154:33–46, "Use of Specific Monoclonal Antibodies and Soluble Receptors".

Browning, Jeffrey and Ngam-ek, Apinya et al., 1993, Cell, 72:847–856, "Lymphotoxin Beta, a Novel Member of the TNGF Family that Forms a Heteromeric Complex with Lymphotoxin on the Cell Surface".

Browning, Jeffrey and Ribolini, Ann, 1989, J. of Immunol., 143:1859–1867, "Studies on the Differing Effects of Tumor Necrosis Factor and Lymphotoxin on the Growth of Several Human Tumor Lines".

Crowne, Paul, VanArsdale, Todd, et al., 1994, J. of Immunol. Methods, 168:79–89, "Production of lymphotoxin (LTalpha) and a Soluble dimeric form of its receptor using the baculovirus expression system".

Crowne, Paul, VanArsdale, Todd et al., 1994, Science, 264:707–710, "A Lymphotoxin Beta Specific Receptor".

Dhein, Jens et al., 1992, J. of Immunol., 149:3166–3173, "Induction of Apoptosis By Monoclonal Antibody Anti–APO–1 Class Switch Variants Is Dependent On Cross–Linking of APO–1 Cell Surface Antigens".

Dighe, Anand et al., 1994, Immunity, 1:447–456, "Enhanced In Vivo Growth and Resistance to Rejectionof Tumor Cells Expressing Dominant Negative IFNy Receptors".

Duzgunes, Nejat et al., 1992, J. of Cell Biochem., 16E:77, "Liposome Targeting To HIV–Infected Cells Via Recombinant Soluble CD4 and CD4–IgG".

(List continued on next page.)

*Primary Examiner*—Geetha P. Bansal
(74) *Attorney, Agent, or Firm*—Niki D. Cox; Biogen, Inc.

(57) ABSTRACT

This invention relates to compositions and methods useful for activating LT-β receptor signaling, which in turn elicits potent anti-proliferative effects on tumor cells. More particularly, this invention relates to lymphotoxin heteromeric complexes formed between lymphotoxin-α and multiple subunits of lymphotoxin-β, which induce cytotoxic effects on tumor cells in the presence of lymphotoxin-β receptor activating agents. Also within the scope of this invention are antibodies directed against the lymphotoxin-β receptor which act as lymphotoxin-β receptor activating agents alone or in combination with other lymphotoxin-β receptor activating agents either in the presence or absence of lymphotoxin-α/β complexes. A screening method for selecting such antibodies is provided. This invention also relates to compositions and methods using cross-linked anti-lymphotoxin-β receptor antibodies either alone or in the presence of other lymphotoxin-β receptor activating agents to potentiate tumor cell cytotoxicity.

5 Claims, 8 Drawing Sheets

OTHER PUBLICATIONS

Eppstein, Deborah, 1985, Proc natl Acad. Sci., 82:3688–3692, "Biological activity of liposome–encapsulated murine interferon y is mediated by a cell membrane receptor".

Fukushima, Keiko et al., 1993, Arch. Biochem. Biophys., 304:144–153, "N–Linked Sugar Chain Structure of Recombinant Human Lymphotoxin Produced by CHO Cells: The Functional Role of Carbohydrate as to Its Lectin–like Character and Clearacne Velocity".

Havell, Edward et al., 1988, J. Exp. Med., 167:1067–1085, "The Anittumor Function of Tumor Necrosis Factor(TNF)".

Hwang et al., 1980, Pro. Natl. Acad. Sci., 77:4030–4034, "Hepatic uptake and degradation of unilamellar sphingomyelin/cholesterol liposomes: A kinetic study".

Johne, Bert et al., 1993, J. Immun.Methods, 160:191–198, "Epitope mapping and binding kinetics of monoclonal antibodies studied by real time biospecific interaction . . . ".

Juraskova, Vera et al., 1992, Eur. J. Pharmacol., 221:107–111, "Interferon inducer, polyribogunanylic polyribocytidylic acid, inhibits experimental hepatic metastases in mice".

Kawabe, Tsutomu et al., 1994, Immunity, 1:167–178, "The Immune Responses in CD40–Deficient Mice: Impaired Immunoglobullin Class . . . ".

Kolanus, Waldemar et al., 1993, Cell, 74:171–183, "T Cell Activation by Clustered Tyrosine Kinases".

Kopp, William C. et al., 1993, J. of Immunother., 13:181–190, "Immunomodulatory Effects of Interferon—y in Patients with Metastatic Malignant Melanoma".

Lane, Peter et al., 1992, Eur. J. Immunol., 22:2573–2578, "Activated human T cells express a ligand for the human B cell–associated antigen CD–40 which participates in T cell–dependent activationof B lymphocytes".

Langer, Robert, 1982, Chemtech. 12:98–105, "Controlled release of macromolecules".

Langer, Robert, Brem, Henry et al., 1981, J. of Blomed. Materials, 15:267–277, "Biocompatibility of polymeric delivery systems for macromolecules".

Ling, Leona et al., 1995, J. of Interferon and Cytokine Res., 15:53–59, "Human Type I Interferon Receptor, IFNAR, Is A Heavily Glycosylated 120–130 kD Membrane Protein".

Loetshcer, Hansruedi et al., 1991, J. of Biolog. Chem., 266:18324–18329, "Recombinant 55–kDa Tumor Necrosis Factor (TNGF) Receptor".

Morrison, Sherle et al., 1984, Pro. Natl. Acad. Sci., 81:6851–6855, "Chimeric human antibody molecules: Mouse antigen–binding domains . . . ".

Niederle, Norbert et al., 1993, Leuk. Lymphoma, 9:111–119, "Long–Term Tretment of Chronic Myaelogenous Leukemia with Different Interferons: Results from Three Studies".

Onishi, Tetsuro et al., 1994, Acta. Urol. Jpn., 40:195–200, "A Study On Direct Antitumor Activity of Bropirimine (Oral Interferon Inducer) For Renal Cell Carcinoma".

Pleskov, V.M. et al., 1994, pp. 125–128, "Receptor–Mediated Endocytosis of Influenza Viruese and Low Density Lipoproteins by Tissue Cells".

Queen, Cary et al., 1989, Proc. Natl. Acad. Sci., 86:10029–10033, "A Humanized antibody that binds to the interleukin 2 receptor".

Raitano, Arthur B. et al., 1990, J. of Biol. Chem., 265:10466–10472, "Tumor Necrosis Factor Up–Regulates y–Interferon Binding in a Human Carcinoma Cell Line".

Schiller, Joan et al., 1991, Cancer Research, 51:1651–1658, "Biological and Clinical Effects of Intravenous Tumor Necrosis Factor–alpha Administered Three Times Weekly".

Schoenfeld, Hans–Joachim et al., 1991, J. of Biol. Chem., 266:3863–3869, "Efficient Purificationof Recombinant Human Tumor Necrosis Facotr *Beta* from *Escherichia coli* Yields Biologically Active Protein with a Trimeric Structure that binds to Both Tumor Necrosis Factor Receptors".

Sidman, Kenneth et al., 1983, Biopolymers, 22:547–556, "Controlled Release of Macromolecules and Pharmaceuticals from Synthetic Polypeptides Based on Glutamic Acids".

Stepushkin, A.N. et al., 1994, pp. 131–134, "Comparative Studies of Live and Inactivated Influenza Vaccines: Organization of the Observations and the Results of Studies of Reactogenicty and Immunogenicity".

Traunecker, Andre et al., 1989, Nature, 339:68–70, "Highly efficient neutralizationof HIV with recombinant CD4–immunoglobulin molecules".

Ullrich, Axel et al., 1990, Cell, 61:203–212, "Signal Transduction by Receptors with Tyrosine Kinase Activity".

Winter, Greg el al., 1991, Nature, 349:293–299, "Man–Made antibodies".

Xu, Jianchao et al., 1994, Immunity, 1:423–431, "Mice Deficient for the CD40 Ligand".

Yonehara, Shin et al., 1989, J. Exp. Med., 169:1747–1756, "A Cell–Killing Monoclonal Antibody (Anti–Fas) To A Cell Surface Antigen Co–Downregulated With The Receptor Of Tumor Necrosis Factor".

LYMPHOTOXIN-α/β COMPLEXES AND ANTI-LYMPOTOXIN-β RECEPTOR ANTIBODIES AS ANTI-TUMOR AGENTS

This application is a 371 of PCT/US96/01386, filed Jan. 26, 1996 which is a continuation-in-part U.S. Ser. No. 08/378,968, filed Jan. 26, 1995.

TECHNICAL FIELD OF THE INVENTION

This invention relates to compositions and methods useful for activating lymphotoxin-β receptor signaling, which in turn elicits potent anti-proliferative effects on tumor cells. More particularly, this invention relates to lymphotoxin heteromeric complexes formed between lymphotoxin-α and multiple subunits of lymphotoxin-β, which induce cytotoxic effects on tumor cells in the presence of lymphotoxin-β receptor activating agents. Also within the scope of this invention are antibodies directed against the lymphotoxin-β receptor which act as lymphotoxin-β receptor activating agents alone or in combination with other lymphotoxin-β receptor activating agents either in the presence or absence of lymphotoxin-α/β complexes. A screening method for selecting such antibodies is provided. This invention also relates to compositions and methods using cross-linked anti-lymphotoxin-β receptor antibodies in the presence of other lymphotoxin-β receptor activating agents to potentiate tumor cell cytotoxicity.

BACKGROUND OF THE INVENTION

The tumor necrosis factor (TNF) receptor family has several members whose signaling can induce tumor cell death by necrosis or apoptosis (programmed cell death). The ligands TNF and lymphotoxin-α (LT-α; formerly called TNF-β) bind to and activate TNF receptors (p60 and p80; herein called "TNF-R"). TNF-R signaling initiates general immune responses to infection or stress in normal cells, but is cytotoxic to cells with transformed phenotypes or to tumor cells. TNF-R signaling can selectively lyse tumor cells and virus-infected cells. The cytotoxic effects of TNF-R signaling on tumor cells are enhanced by interferon-γ and by a variety of conventional chemotheropeutic agents.

It would be useful to take advantage of the anti-proliferative or cytotoxic activities induced by TNF-R signaling in tumor cells for therapeutic purposes. However, TNF-R activation has pleiotropic effects on a variety of immunoregulatory responses including the initiation of proinflammatory cascades. Thus it has not been possible to direct the cytotoxic effects of TNF-R signaling to tumor cells without co-stimulating inflammatory responses which lead to general toxicity in humans.

Similarly, stimulation of another TNF-related receptor called the Fas receptor (FasR) can trigger cytotoxicity by programmed cell death in a variety of both tumor and non-tumor cell types. However, FasR activation has been shown to cause rapid liver necrosis, thus precluding its therapeutic application in humans.

Recently, another receptor in the TNF family called the LT-β receptor (LT-β-R) was identified (Crowe et al., *Science*, 264, pp. 707–10 (1994). The LT-β-R binds heteromeric lymphotoxin complexes (LT-α/β) which comprise LT-α subunits in association with another TNF-related polypeptide called lymphotoxin-β (LT-β). These LT-α/β complexes are membrane-associated and most have a LT-α1/β2 stoichiometry (Browning et al., *Cell*, 72, pp. 847–56 (1993); Browning et al., *J. Immunol.*, 154, pp. 33–46 (1995)).

By analogy to TNF-R and other TNF-like receptors, the activation of LT-β-R signaling is thought to occur when multiple receptors on the cell surface are brought into close proximity (Crowe et al., *Science*, 264, pp. 707–10 (1994)). This process is referred to as receptor clustering. The TNF and LT ligands are multivalent complexes which can simultaneously bind to and thus aggregate more than one receptor. Receptor clustering as a means for receptor activation in other systems has been well-documented, especially for receptor tyrosine kinases (Ullrich and Schlessinger, *Cell*, 61, pp. 203–212 (1990); Kolanus et al., *Cell*, 74, pp. 171–83 (1993)). Accordingly, administering LT-α1/β2 ligands and/or LT-β-R activating agents which can induce the clustering and downstream signaling of LT-β-R molecules on the surface of target tumor cells would be useful for directly stimulating the LT-β-R pathway in these cells.

Signaling by LT-β-R, like TNF-R, can activate pathways that lead to cytotoxicity and cell death in tumor cells. Importantly, LT-α1/β2 ligands do not bind to TNF-R with any significant affinity. For this reason, directed LT-β-R activation in tumor cells would trigger cytotoxicity in those cells without stimulating the inflammatory pathways associated with TNF-R activation. Treatment with LT-α1/β2 and/or other LT-β-R activating agents would thus be useful for treating or reducing the advancement, severity of effects of tumorigenic cells (neoplasia) while overcoming the potent side effect problems which have been encountered when TNF-R or FasR activation has been tried as an anti-tumor treatment.

SUMMARY OF THE INVENTION

The present invention solves the problems referred to above by providing pharmaceutical compositions and methods for treating tumor cells by stimulating LT-β-R signaling without co-stimulating TNF-R-associated inflammatory responses. In one embodiment, lymphotoxin complexes formed between LT-α and multiple subunits of LT-β are provided (LT-α/β heteromeric complexes) which induce cytotoxic effects on cells bearing the LT-β-R in the presence of a LT-β-R activating agent. The preferred compositions and methods of this embodiment comprise LT-α1/β2 complexes in the presence of a LT-β-R activating agent. More preferably, the LT-α1/β2 complexes are in a soluble rather than a membrane-bound form, and the LT-β-R activating agent is IFN-γ.

In another embodiment of the invention, at least one antibody directed against LT-β-R (anti-LT-β-R Ab) is used as a second LT-β-R activating agent in conjunction with the LT-α/β heteromeric complex. The preferred compositions and methods of this embodiment are characterized by LT-α1/β2 in the presence of IFN-γ as a first activating agent, and at least one anti-LT-β-R Ab as a second LT-β-R activating agent. More preferably, the LT-α1/β2 complexes are soluble and the antibody is a monoclonal antibody (anti-LT-β-R mAb).

In another embodiment of the invention, at least one anti-LT-β-R Ab in the presence or absence of a second LT-β-R activating agent is used without an exogenous LT-α/β heteromeric complex. The preferred compositions and methods of this embodiment comprise at least two anti-LT-β-R monoclonal antibodies (anti-LT-β-R mAbs) which recognize non-overlapping epitopes of LT-β-R in combination with IFN-γ.

In a further embodiment, this invention provides pharmaceutical compositions and methods for potentiating tumor cell cytotoxicity characterized by cross-linked anti-LT-β-R Abs used conjunction with a second LT-β-R activating agent. In one preferred embodiment, individual anti-LT-β-R Abs are immobilized by cross-linking them onto a surface. In another preferred embodiment, the anti-LT-β-R Abs are cross-linked in solution. More preferably, the anti-LT-β-R Abs are monoclonal antibodies and the second LT-β-R activating agent is IFN-γ.

This invention further provides a novel screening process for selecting LT-β-R activating agents, such as anti-β-R Abs, that function in combination with LT-α/β heteromeric complexes to promote tumor cell death. The assay makes use of the increased sensitivity of human adenocarcinoma cells to LT-α/β heteromeric complexes in the presence of LT-β-R activating agents in a cytotoxicity assay. The procedure used to test putative LT-β-R activating agents is exemplified for the case of anti-LT-β-R antibodies, and comprises the following steps:

1) Tumor cells (e.g. HT29 human adenocarcinoma cells) are cultured for several days in media containing IFN-γ and purified LT-α1/β2 in the presence or absence of the particular anti-LT-β-R Ab being assayed;
2) The cells are treated with a dye that stains living cells; and
3) The number of stained cells is quantitated to determine the fraction of tumor cells killed in the presence of the LT-α1/β2, IFN-γ and the test anti-LT-β-R Ab in each sample. Alternatively, the number of surviving cells can be determined by any of a number of well-known assays which measure cell viability, such as $^3$H-thymidine incorporation into DNA.

An anti-LT-β-R Ab (or an Ab combination) which significantly increases the percentage of tumor cells killed in this assay is a LT-β-R activating agent within the scope of this invention. This cytolytic assay can be adapted to identify new LT-β-R activating agents which function in combination with LT-α/β heteromeric complexes.

DETAILED DESCRIPTION OF THE INVENTION

Figure 1A:
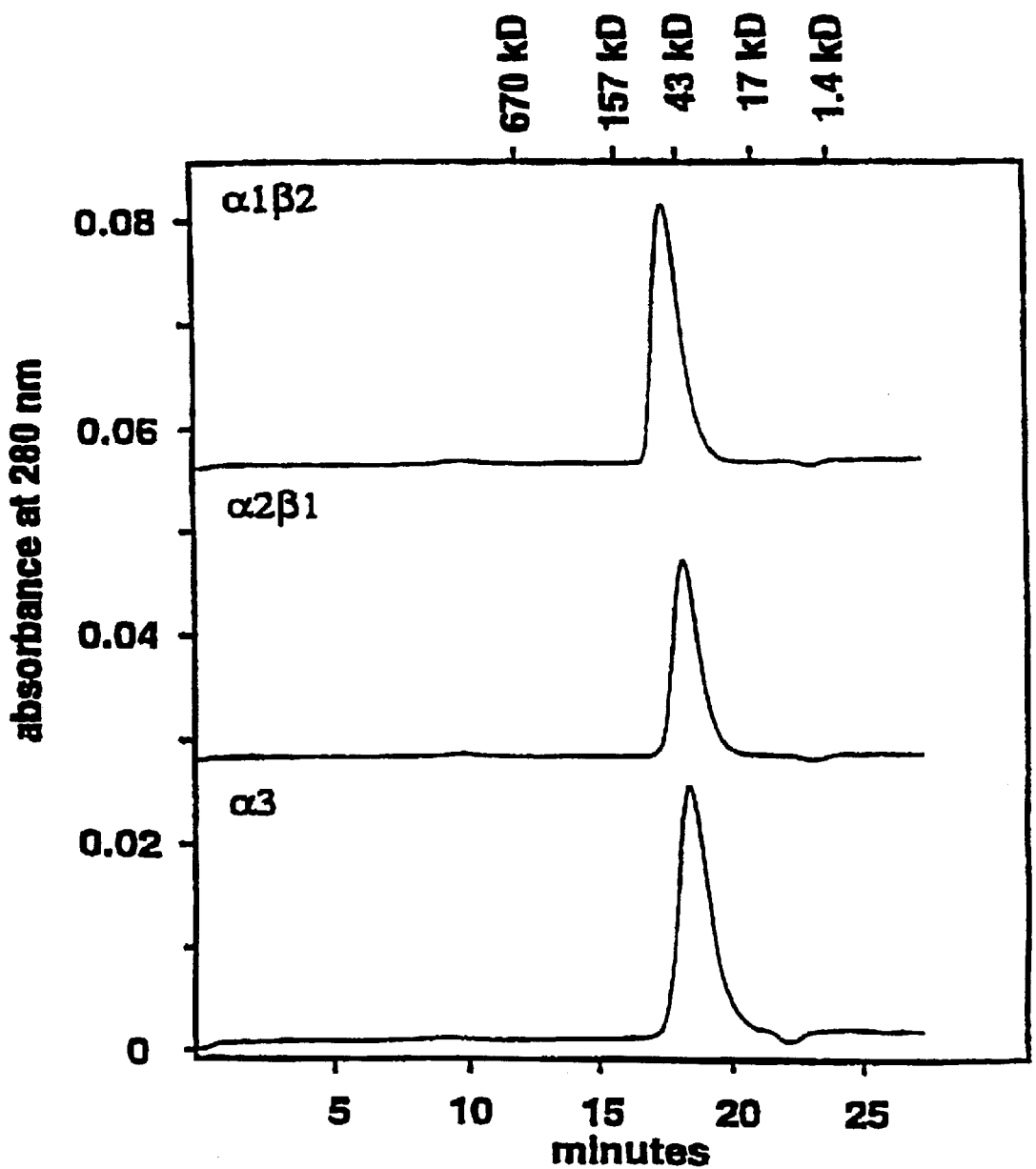
FIG. 1A. Sizing analyses of the purified LT-α/β heteromeric complex forms separated by TNF-R and LT-β-R immunoaffinity chromatography. Purified proteins were analyzed on a TSK 3000 HPLC resin in phosphate-buffered saline. The position of various size markers is shown.

In order that the invention herein described may be fully understood, the following detailed description is set forth.

The term "anti-tumor activity" refers to the ability of a substance or composition to block the proliferation of, or to induce the death of tumor cells which interact with that substance or composition.

The term "apoptosis" refers to a process of programmed cell death.

The term "cytotoxic activity" refers to the ability of a substance or composition to induce the death of cells which interact with that substance or composition.

The term "epitope" (or antigenic determinant) is defined as the part of a molecule that combines with a single antigen binding site on an antibody molecule. A single epitope is recognized by a monoclonal antibody (mAb). Multiple epitopes are normally recognized by polyclonal antibodies (Ab).

The "Fc domain" of an antibody refers to a part of the molecule comprising the CH2, CH3 and hinge regions but lacking the antigen binding sites.

The term "interferon inducing agent" refers to any agent which is capable of directly or indirectly stimulating the endogenous production of either type I (IFN-α, IFN-β) or type II (IFN-γ) interferons. Examples of interferon inducing agents include double stranded RNA molecules, and a variety of plant or pharmaceutically-derived compounds.

The terms "LT-α mutein" and "LT-β mutein" refer to LT-α or LT-β polypeptides having one or more amino acid changes compared to the amino acid sequence of the corresponding native polypeptide.

The term "LT-β-R activating agent" refers to any agent which can augment ligand binding to LT-β-R, cell surface LT-β-R clustering or LT-β-R signaling, or which can influence how the LT-β-R signal is interpreted within the cell. Examples of LT-β-R activating agents include, IFN-α, IFN-γ, TNF, interferon inducing agents, soluble anti-LT-β-R Abs, cross-linked anti-LT-β-R Abs and multivalent anti-LT-β-R Abs.

The term "LT-β-R signaling" refers to all molecular reactions associated with the LT-β-R pathway and subsequent molecular reactions which result therefrom.

The term "anti-LT-β-receptor antibody" ("anti-LT-β-R Ab") refers to any antibody that recognizes and binds to at least one epitope of the LT-β receptor.

The term "anti-LT-β receptor monoclonal antibody" ("anti-LT-β-R mAb") refers to any monoclonal antibody that recognizes and binds to a single epitope of the LT-β-R.

The term "cross-linked anti-LT-β-R (m)Abs" refer to antibodies directed against the LT-β-R which have either been cross-linked to each other to form antibody agglomerates in solution using an anti-LT-β-R antibody (Ab) or (mAb) cross-linking agent, or which have been immobilized in close proximity to one another on a surface or matrix.

The term "anti-LT-β-R Ab (or mAb) cross-linking agent" refers to any agent which can covalently or non-covalently aggregate anti-LT-β-R Abs in solution so that the Abs can bind to and potentiate target cell surface LT-β receptor clustering. Such cross-linking agents include but are not limited to chemical cross-linking agents, secondary antibodies which react with portions of the anti-LT-β-R Abs or mAbs, and soluble or surface-bound Fc receptors—either endogenous or added exogenously—which can bind to anti-LT-βR Abs.

The terms "LT-α biological activity", "LT-β biological activity", and "LT-α/β biological activity" are defined as: 1) immunological cross-reactivity with an antibody directed against at least one epitope of the corresponding native subunit or complex or subunits; or 2) the ability of the LT subunit or complex of subunits to compete for ligand binding sites on a LT-specific receptor such as TNF-R or LT-β-R; or 3) having the ability to stimulate an immune regulatory response or cytotoxic activity qualitatively in common with a native LT subunit or complex.

The term "LT-α/β heteromeric complex" refers to a stable association between at least one LT-α subunit and more than one LT-β subunits. The subunits can associate through electrostatic, van der Waals, or covalent interactions. Preferably, the LT-α/β heteromeric complex has at least two adjacent LT-β subunits and lacks adjacent LT-α subunits. Most preferably, the complex has the stoichiometry LT-α1/β2.

The term "multivalent ligand" refers to a molecule or complex which has more than one receptor binding site and which is capable of simultaneously binding and bringing into close proximity at least two receptor molecules.

A "type I leader sequence" is an amino-terminal portion of a eukaryotic protein which serves as a signal to direct the protein to the endoplasmic reticular (ER) membrane and often through the entire secretion pathway. The leader sequence is usually cleaved off by a signal peptidase in the ER membrane.

A "signal sequence" is the functional equivalent of a eukaryotic type I leader sequence in prokaryotic hosts, and directs the translocation of proteins into or across lipid bilayer membranes of a bacterium.

A "soluble LT-α/β heteromeric complex" is a LT-α/β heteromeric complex comprising soluble LT-β subunits, wherein the amino acid sequences which localize the polypeptide to the membrane have been deleted or inactivated, rendering the LT-β subunit soluble. Soluble LT-α/β heteromeric complexes can be secreted by an appropriate host cell which has been engineered to express both subunits.

A "surface LT-α/β complex" is a complex comprising LT-α and membrane-bound LT-α subunits which is displayed on the cell surface.

Production of Membrane-bound LT-α/β Complexes

Cell surface lymphotoxin complexes have been characterized in CD4$^+$ T cell hybridoma cells (II-23.D7) that express high levels of LT (Browning et al. *J. Immunol.*, 147, pp. 1230–37 (1991); Androlewicz et al., *J. Biol. Chem.*, 267, pp. 2542–47 (1992)). Mature LT-α lacks a transmembrane domain and is localized to the cell surface through interaction with at least one membrane-bound LT-β subunit. Membrane-bound (surface) LT-α/β heteromeric complexes have predominantly a LT-α1/β2 stoichiometry.

LT-β as a cell membrane protein binds LT-α during synthesis, thus "targeting" the LT-α to the cell membrane. In the absence of LT-β, LT-α is secreted into the extracellular medium. LT subunits normally assemble into complexes inside the cell prior to protein export into the membrane. Once LT-β subunits are inserted into the membrane, they do not form stable complexes with secreted LT-α. Thus if the membrane-bound form of a LT-α/β heteromeric complex is desired, it is preferable to co-express the desired LT-α and LT-β subunits within the same cell.

The surface LT-α/β heteromeric complex can be reconstructed by co-transfection of host cells with both the LT-α and LT-β genes. Surface LT complexes cannot be observed on stable cell lines which express either LT gene alone. However, if the host cell normally produces large amounts of LT-α (e.g. RPMI 1788 cells; see below), then transfection with a LT-β gene with encodes the desired LT-β polypeptide should be sufficient to generate LT-α/β complexes comprising full-length LT-α subunits.

Co-expression of LT-α and LT-β polypeptides in a number of eukaryotic expression systems leads to their assembly and export as active ligand (Crowe et al., *J. Immunol. Methods*, 168, 79–89 (1994)). Host systems that can be used include but are not limited to CHO cells, COS cells, B cells including myelomas, baculovirus-infected insect cells and yeast.

The LT-α subunit of the LT-α/β heteromeric complexes of this invention can be selected from lymphotoxin-α, native human or animal lymphotoxin-α, recombinant lymphotoxin-α, soluble lymphotoxin-α, secreted lymphotoxin-α, lymphotoxin-α muteins having LT-α biological activity, or lymphotoxin-α fragments of any of the above having LT-α biological activity.

The LT-α polypeptide can be any soluble form of the molecule including active fragments thereof which can be produced in eukaryotic expression systems, wherein the natural LT-α leader sequence will be cleaved off. Alternatively, fusions of the mature LT-α sequence with a heterologous signal sequence can be used to maximize the secretion of LT-α in other host systems. Signals are chosen based on the intended host cell, and may include bacterial, yeast, mammalian and viral sequences. The native signal, or the vascular cell adhesion molecule-1 (VCAM-1) signal sequence is suitable for use in mammalian expression systems.

LT-α polypeptides can also be fused to polypeptides having a prolonged plasma half-life such as immunoglobulin chains or fragments thereof. Plasma proteins which may be used to enhance plasma half-life include serum albumin, immunoglobulins, apolipoproteins, and transferrin. Polyethylene glycol (PEG) attachment may stabilize the polypeptide and lower its immunogenicity. Preferably the LT-α fusion protein is not significantly immunogenic in the subject to be treated and the plasma protein does not cause undesirable side effects in subjects due to its normal biological activity.

Human LT-α is glycosylated on N and O residues, and depending on the source, exhibits considerable sugar-based microheterogeneity. The oligosaccharide composition of the particular LT-α chosen to form the LT complex may affect in vivo clearance rates (Fukushima et al., *Arch. Biochem. Biophys.*, 304, pp. 144–53 (1993)). Since glycosylation variants can be produced by expression in different host cells, this is one factor to be considered in selecting a source of LT-α.

LT-α can be purified from a B lymphoblastoid line RPMI 1788, which constitutively secretes LT-α and which can be induced to secrete higher levels by treating with the phorbol ester PMA (Aggarwal et al., *J. Bio. Chem.*, 259, pp. 686–91 (1984)). Alternatively, the cloned human LT-α gene can be used to recombinantly produce LT-α polypeptides in different host systems including bacteria (Schoenfeld et al., *J. Biol. Chem.*, 266, pp. 3863–69 (1991)); baculovirus-infected insect cells (Crowe et al., *J. Immunol. Methods*, 168, pp. 70–89 (1994)); and mammalian cells (Browning and Ribolini, *J. Immunol.*, 143, pp. 1859–67 (1989); Fukushima et al., *Arch. Biochem. Biophys.*, 304 pp. 144–53 (1993)).

Portions of the LT-α gene which encode polypeptide fragments having LT-α biological activity can be evaluated using routine screening assays. Useful screening assays for LT-α biological activity include competitive inhibition assays with native LT-α bound to TNF-R, or measuring either directly or indirectly by inhibition the ability of the LT-α to induce cytotoxicity of tumor cells in assays known to the art. Preferably, LT-α fragments are assembled into heteromeric complexes with LT-β and the complexes assayed for LT-α/β biological activity by competitive inhibition with LT-α/β bound to LT-β-R, or for their ability to induce cytotoxicity of tumor cells in the assays disclosed herein.

Lymphotoxin-β, also referred to as p33, has been identified on the surface of T lymphocytes, T cell lines, B cell lines and lymphokine-activated killer cells. LT-β is the subject of applicants' co-pending international applications PCT/US91/04588, published Jan. 9, 1992 as WO 92/00329; and PCT/US93/11669, published Jun. 23, 1994 as WO 94/13808, which are herein incorporated by reference.

The LT-β gene encodes a polypeptide of 240–244 amino acids (Browning et al., *Cell*, 72, pp. 847–56 (1993)). LT-β is a type II membrane protein with a short N-terminal cytoplasmic domain followed by a membrane anchoring domain of 30 hydrophobic amino acids. It has a single N-linked glycosylation site and has only one cysteine residue which does not appear to be involved in intersubunit disulfide bond formation.

The LT-β subunits comprising the LT-α/β heteromeric complexes of the present invention can be selected from lymphotoxin-β, native human or animal lymphotoxin-β, recombinant lymphotoxin-β, soluble lymphotoxin-β, secreted lymphotoxin-β, lymphotoxin-β muteins having LT-β biological activity, or lymphotoxin-β fragments of any of the above having LT-β biological activity.

As discussed above for the LT-α polypeptide, the LT-β polypeptides can also be modified to increase their solubility or plasma half-life using the same methods. Likewise, portions of the LT-β gene which encode polypeptide fragments having LT-β biological activity can be evaluated using routine screening assays as discussed for LT-α.

Production of soluble complexes

Soluble (non-membrane-bound) LT-α/β heteromeric complexes comprise LT-β subunits which have been changed form a membrane-bound to a soluble form. These complexes are described in detail in applicants' co-pending international application (PCT/US93/11669, published Jan. 9, 1992 as WO 94/13808). Soluble LT-β peptides are defined by the amino acid sequence of lymphotoxin-β wherein the sequence is cleaved at any point between the end of the transmembrane region (i.e. at about amino acid #44) and the first TNF homology region (i.e. at amino acid #88) according to the numbering system of Browning et al., *Cell*, 72, pp. 847–56 (1993).

Soluble LT-β polypeptides may be produced by truncating the N-terminus of LT-β to remove the cytoplasmic tail and transmembrane region (Crow et al., *Science*, 264, pp. 707–710 (1994). Alternatively, the transmembrane domain may be inactivated by deletion, or by substitution of the normally hydrophobic amino acid residues which comprise a transmembrane domain with hydrophilic ones. In either case, a substantially hydrophilic hydropathy profile is created which will reduce lipid affinity and improve aqueous solubility. Deletion of the transmembrane domain is preferred over substitution with hydrophilic amino acid residues because it avoids introducing potentially immunogenic epitopes.

The deleted or inactivated transmembrane domain may be replaced with or attached to a type I leader sequence (e.g. the VCAM-1 leader) such that the protein is secreted beginning with a sequence anywhere from between va140 to pro88. Soluble LT-β polypeptides may include any number of well-known leader sequences at the N-terminus. Such a sequence would allow the peptides to be expressed and targeted to the secretion pathway in a eukaryotic system. See, e.g., Ernst et al., U.S. Pat. No. 5,082,783 (1992).

Soluble LT-α/β heteromeric complexes may be produced by co-transfecting a suitable host cell with DNA encoding LT-α and soluble LT-β (Crow et al., *J. Immunol. Methods*, 168, pp. 79–89 (1994)). Soluble LT-β secreted in the absence of LT-α is highly oligomerized. However, when co-expressed with LT-α, a 70 kDa trimeric-like structure is formed which contains both proteins. It is also possible to produce soluble LT-α1/β2 heteromeric complexes by transfecting a cell line which normally expresses only LT-α (such as the RPMI 1788 cells discussed above) with a gene encoding a soluble LT-β polypeptide.

LT-α and LT-β polypeptides may be separately synthesized, denatured using mild detergents, mixed together and renatured by removing the detergent to form mixed LT heteromeric complexes which can be separated (see below).

Purification of LT-α1/β2 Complexes

Soluble LT-α1/β2 heteromeric complexes are separated from co-expression complexes comprising a different subunit stoichiometry by chromatography using TNF and LT-β receptors as affinity purification reagents. The TNF receptors only bind within α/α clefts of LT complexes. The LT-β receptor binds with high affinity to β/β clefts, and with lower affinity to α/β clefts of heteromeric LT-α/β complexes. Accordingly, LT-α3 and LT-α2/β1 will bind to TNF-R. The LT-β-R can also bind LT-α2/β1 trimers (within the α/β clefts) but cannot bind LT-α3. In addition, the LT-β-R (but not TNF-R) binds LT-α1/β2 and LT-βn (the exact composition of such preparation is unknown, however, they are large aggregates).

The receptor affinity reagents can be prepared as either a soluble extracellular domain (see for example Loetscher et al., *J. Biol. Chem.*, 266, pp. 18324–29 (1991)), or as chimeric proteins with the extracellular ligand binding domain coupled to an immunoglobulin Fc domain (Loetscher et al., *J. Biol. Chem.*, 266, pp. 18324–29 (1991); Crowe et al., *Science*, 264, pp. 707–710 (1994)). Receptors are coupled to affinity matrices by chemical cross-linking using routine procedures.

There are two schemes by which the LT-α1/β2 ligand can be purified using receptors and immuno-affinity chromatography. In the first scheme, a supernatant from an appropriate expression system co-expressing both LT-α and the truncated LT-β form is passed over a TNF-R column. The TNF-R will bind LT-β3 and LT-α2/β1 trimers. The flow through from the TNF-R column will contain LT-β(n) and LT-α1/β2.

In the second scheme, all LT-β-containing forms (LT-β(n), LT-α1/β2 and LT-α2/β1) are bound to and eluted from a LT-β-R column using classical methods such as chaotrophe or pH change. (LT-α3 flows through this column). The eluate is neutralized or the chaotrophe removed, and the eluate is then passed over a TNF-R column, which binds only to the LT-α2/β1 trimers. The flow through of this column will contain LT-β(n) and LT-α1/β2 trimers.

In both cases, pure LT-α1/β2 trimers can be separated from LT-β by subsequent gel filtration and/or ion exchange chromatographic procedures known to the art.

Alternatively, different forms of LT-α/β heteromeric complexes can be separated and purified by a variety of conventional chromatographic means. It may also be preferable to combine a series of conventional purification schemes with one of the immunoaffinity purification steps described above.

Source of Anti-LT-β-R Antibodies

Polyclonal antibody sera directed against the human LT-β receptor are prepared using conventional techniques by injecting animals such as goats, rabbits or mice subcutaneously with a human LT-β receptor-Fc fusion protein (Example 2) in complete Freund's adjuvant, followed by booster intraperitoneal or subcutaneous injection in complete Freunds. Polyclonal antisera containing the desired antibodies which are directed against the LT-β receptor are screened by conventional procedures.

Mouse monoclonal antibodies (mAbs) directed against a human LT-β receptor-Fc fusion protein are prepared by intraperitoneal immunization of RBF mice repetitively with a CHO cell-derived recombinant LT-β receptor-Fc fusion protein (LT-β-R -Fc) attached to protein A sepharose beads in the absence of adjuvant. Animals are finally boosted with soluble LT-β-R-Fc (both i.p. and i.v.), spleen cells are fused using classical protocols, and hybridomas are screened by ELISA (Ling et al., *J. Interferon and Cytokine Res.*, 15, pp. 53–59 (1995)). Hybridomas are further screened for their ability to block binding of activated II-23 hybridoma cells—which express surface LT-α1/β2—to LT-β-R-Fc-coated plates in a cell panning assay. Pure mAbs are prepared by protein A sepharose purification of IgG from hybridoma culture supernatants.

Various forms of anti-LT-β-R antibodies can also be made using standard recombinant DNA techniques (Winter and Milstein, *Nature*, 349, pp. 293–99 (1991)). For example, "chimeric" antibodies can be constructed in which the antigen binding domain from an animal antibody is linked to a human constant domain (e.g. Cabilly et al., U.S. Pat. No. 4,816,567; Morrison et al., *Proc. Natl. Acad. Sci. U.S.A.*, 81, pp. 6851–55 (1984)). Chimeric antibodies reduce the observed immunogenic responses elicited by animal antibodies when used in human clinical treatments.

In addition, recombinant "humanized antibodies" which recognize the LT-β-R can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject.

Construction of different classes of recombinant anti-LT-β-R antibodies can also be accomplished by making chimeric or humanized antibodies comprising the anti-LT-β-R variable domains and human constant domains (CH1, CH2, CH3) isolated from different classes of immunoglobulins. For example, anti-LT-β-R IgM antibodies with increased antigen binding site valencies can be recombinantly produced by cloning the antigen binding site into vectors carrying the human μ chain constant regions (Arulanandam et al., *J. Exp. Med.*, 177, pp. 1439–50 (1993); Lane et al., *Eur. J. Immunol.*, 22, pp. 2573–78 (1993); Traunecker et al., *Nature*, 339, pp. 68–70 (1989)).

In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling (Queen et al., *Proc. Natl. Acad. Sci. U.S.A.*, 86, pp. 10029–33 (1989); WO 94/04679).

It may be desirable to increase or to decrease the affinity of anti-LT-β-R Abs for the LT-β-R depending on the targeted tissue type or the particular treatment schedule envisioned. For example, it may be advantageous to treat a patient with constant levels of anti-LT-β-R Abs with reduced ability to signal through the LT-β pathway for semi-prophylactic treatments. Likewise, anti-LT-β-R Abs with increased affinity for the LT-β-R may be advantageous for short-term, tumor-targeted treatments.

Screening Anti-LT-β-R Antibodies For LT-β-R Activating Agents

The anti-LT-β-R antibodies of this invention can potentiate the anti-tumor activity of LT-α/β heteromeric complexes (preferably LT-α1/β2) in the presence of an LT-β-R activating agent such as IFN-γ. These anti-LT-β-R antibodies are also referred to herein as LT-β-R activating agents. The antibodies which act as LT-β-R activating agents are selected as follows:

1) A series of tissue culture wells containing tumor cells such as HT29 cells are cultured for three to four days in media containing a LT-β-R activating agent such as INF-γ, and purified LT-α/β heteromeric complex—preferably LTα1/β2—in the presence or absence of serial dilutions of the anti-LT-β-R Ab being tested;

2) A vital dye stain which measures mitochondrial function such as MTT is added to the cell mixture and reacted for several hours;

3) The optical density of the mixture in each well is quantitated at 550 nm wavelength light (OD 550). The OD 550 is inversely proportional to the number of tumor cells killed in the presence of the LT-α/β heteromeric complex, the LT-β-R activating agent and test anti-LT-β-R Ab in each well.

The preferred antibodies of this invention which act individually as LT-β-R activating agents in the presence of LT-α1/β2 and IFN-γ include the BKA11, CDH10, BHA10 and BCG6 anti-LT-β-R mAbs (Table 2, infra).

Cross-linking Anti-LT-β-R Antibodies

The cross-linked anti-LT-β-R antibodies of this invention act individually as LT-β-R activating agents without exogenous LT-α/β heteromeric complexes in the presence of a second LT-β-R activating agent such as IFN-γ. Cross-linked anti-LT-β-R Abs apparently bind to and induce clustering of cell surface LT-β receptors thereby activating LT-β receptor-mediated targeted cell death.

In one embodiment, one or more types of anti-LT-β-R antibodies are cross-linked by immobilization onto a water-insoluble matrix or surface. Derivatization with a bifunctional agent is useful for cross-linking the antibodies to the water-insoluble support matrix or surface. Agents commonly used to effect cross-linking of antibodies to a water insoluble support matrix or surface include 1,1 bis(-diazoacetyl)-2-phenylethane, glutyraldehyde, N-hydroxysuccinamide esters including esters with 4-azidosalicylic acid, homobifunctional imidoesters including disuccinimidyl esters, and bifunctional maleimides such as bis-N-maleimido-1,8-octane. Derivatizing agents such as methyl-3-[(p-azidophenyl) dithio] propioimidate form photoactivatable intermediates which can be selectively cross-linked when stimulated with light. Reactive water-insoluble matrices such as cyanogen bromide-activated carbohydrates and the substrates described in U.S. Pat. Nos. 3,959,080; 3,969,287; 3,691,016; 4,195,128; 4,247,642; 4,229,537; 4,055,635; and 4,330,440 can also be used for protein immobilization and cross-linking.

The surfaces to which the antibodies are attached can be non-proteinaceous polymer, usually a hydrophilic polymer either from natural or synthetic sources. Hydrophilic polyvinyl polymers such as polyvinylalcohol (PVA) and polyvinylpyrrolidone (PVP) can be used. Also useful are polyalkylene ethers such as polyethylene glycol, polypropylene glycol, polyoxyethylene esters or methoxy polyethylene glycol, polyoxyalkylenes such as polyoxyethylene and polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. poly-mannuronic acid or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopoly-saccharides, e.g. hyaluronic acid; polymers of sugar alcohols such as polysorbitol and polymannitol; and heparin or heparon.

The polymer prior to cross-linking is preferably water soluble and preferably contains only a singly reactive chemical group to avoid multiple cross-linking events with the antibody. In any case, reaction conditions should be optimized to reduce cross-linking and to recover products—either directly or by a subsequent gel filtration or chromatographic step—having a substantially homogenous molecular weight range. The optimal molecular weight of the cross-linked antibody matrix will be determined by routine experimentation using the cytotoxicity and receptor binding assays disclosed herein.

The final conjugate after cross-linking is preferably soluble in physiological fluids such as blood. The polymer should not be highly immunogenic in the conjugate form, and should possess a viscosity compatible with intravenous infusion or injection if either is an intended route of administration.

The polymer may also be water insoluble. Materials which may be used include hydrophilic gels, or shaped articles having surfaces to which the antibodies can be immobilized such as surgical tubing, catheters, or drainage conduits. It is preferable to use solid support materials which are biologically compatible and substantially inert in physiological surroundings. A material is biologically compatible if it does not substantially stimulate immune responses including inflammation, or attract fibrotic cells when placed inside the body of a subject.

Anti-LT-β-R Abs may also be immobilized onto surfaces which have been covalently or non-covalently coated with secondary antibodies that will bind to the primary anti-LT-β-R Abs (e.g., goat anti-mouse IgG antibodies; see Example 7). Each anti-LT-β-R mAb tested individually, when immobilized onto a surface with secondary antibodies, acts as an LT-β-R activating agent in the presence of IFN-γ (FIGS. 4 and 7).

In an alternative embodiment, cross-linked anti-LT-β-R Abs in solution act as LT-β-R activating agents. Anti-LT-β-R Abs can be cross-linked by means of an anti-LT-β-R Ab (or mAb) cross-linking agent. An anti-LT-β-R Ab (or mAb) cross-linking agent according to this invention is any agent capable of either covalently linking, or of non-covalently aggregating the anti-LT-β-R Abs (or mAbs) in solution so that the cross-linked anti-LT-β-R Abs (or mAbs) can bind to and potentiate target cell surface LT-β-R clustering. Such anti-LT-β-R Ab (or mAb) cross-linking agents include but are not limited to chemical cross-linking reagents which can be reacted with the antibodies in a controlled manner as described above. Alternatively, secondary antibodies, Sepharose A, Fc receptors, or other agents that will bind to and aggregate multiple primary anti-LT-β-R Abs without blocking their activity can be used to form anti-LT-β-R Abs agglomerates in solution.

Multiple Anti-LT-β-R Abs In Solution Act As LT-β-R Activating Agents

Compositions comprising multiple anti-LT-β-R Abs in solution which act as LT-β-R activating agents by potentiating surface LT-β-R clustering are provided by this invention. Polyclonal anti-LT-β-R Abs directed against different epitopes of the LT-β-R can be used. Preferably, the anti-LT-β-R Abs are monoclonal Abs directed against different and non-overlapping epitopes of the LT-β-R.

The combined anti-LT-β-R mAb approach to LT-β receptor activation requires combining two non-overlapping epitopes. Moreover, it is likely that productive receptor aggregation is only achieved with certain epitopes. We have identified the presence of at least four unique LT-β-R immunoreactive epitopes. Additional epitopes (as defined by new mAbs) may be identified by continuing to fuse immunized mouse spleen cells, by immunizing different species of animals, and by using different routes of immunization.

Epitopes can also be directly mapped by assessing the ability of different mAbs to compete with each other for binding to the LT-β-R using BIAcore chromatographic techniques (Pharmacia BIAtechnology Handbook, "Epitope Mapping", Section 6.3.2, (May 1994); see also Johne et al., *J. Immunol. Methods*, 160, pp. 191–8 (1993)).

Individual LT-β-R mAbs can be grouped into at least four classes according to their ability to cooperate in combination with other LT-β-R mAbs in killing tumor cells in cytolytic assays (Example 8; Table 1). For example, the BDA8 mAb in Group I to promote tumor cell cytotoxicity. Likewise, the Group III BKA11 and CDH10 mAbs do not cooperate in a tumor cell cytotoxicity assay.

Figure 5A:
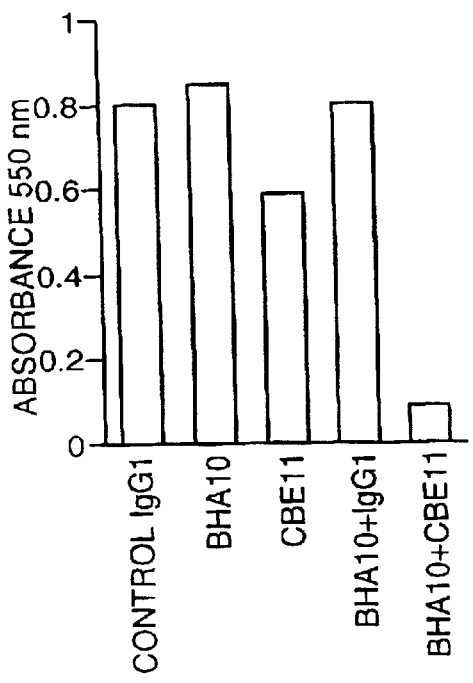
FIG. 5. Representative quantitation of the enhanced cytotoxicity to tumor cells by treating with pairs of soluble anti-LT-β-R mAbs. (A) The cytotoxic effects on HT29 cells of control IgG1 (100 ng/ml), anti-LT-β-R mAb BHA10 (100 ng/ml), anti-LT-β-R mAb CBE11 (50 ng/ml), BHA10 (100 ng/ml)+IgG (100 ng/ml), and BHA10 (100 ng/ml)+CBE11 (50 ng/ml). IFN-γ was present at 80 U/ml. (B) The cytotoxic effects on HT29 cells of control IgG1 (100 ng/ml), anti-LT-β-R mAb CDH10 (100 ng/ml), anti-LT-β-R mAb CBE11 (50 ng/ml), CDH10 (100 ng/ml)+IgG1 (100 ng/ml), and CDH10 (100 ng/ml)+CBE11 (50 ng/ml). IFN-γ was present at 80 U/ml. (C) The cytotoxic effects on HT29 cells of control IgG1 (100 ng/ml), anti-LT-β-R mAb CDH10 (33 ng/ml), anti-LT-β-R mAb AGH1 (50 ng/ml), and CDH10 (33 ng/ml)+AGH1 (50 ng/ml) on HT29 cells IFN-γ was present at 80 U/ml. (D) As in (C), except that WiDr human adenocarcinoma cells were used in the cytolytic assay (Raitano and Korc, *J. Biol. Chem.*, 265, pp. 10466–472 (1990)).
Figure 5B:
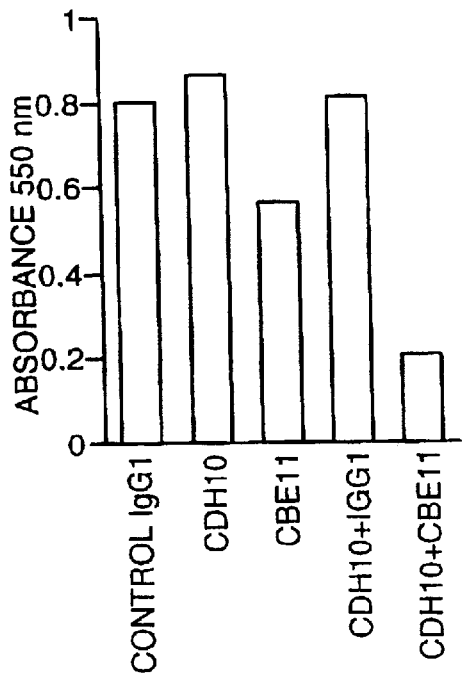
Figure 5C:
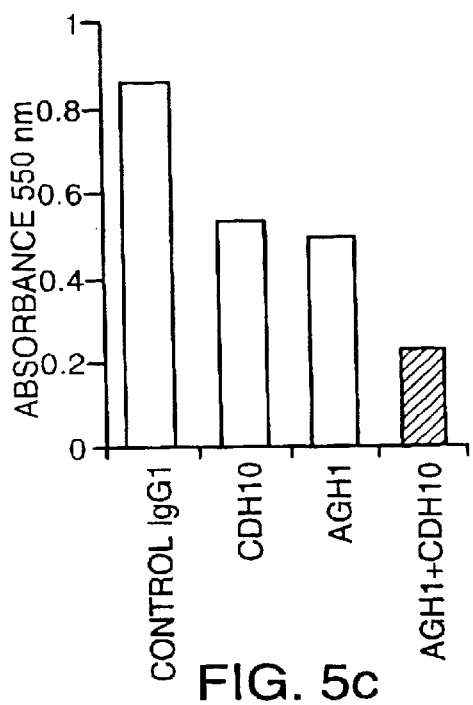

FIG. 5A–C shows the effects of administering representative anti-LT-β-R mAbs alone and in pairwise combination to tumor cells in cytotoxicity assays in the presence of IFN-γ as a LT-β-R activating agent. The Group IV anti-LT-β-R mAb CBE11 used alone has a slight cytotoxic effect which is enhanced in combination with the Group II mAb BHA10 (FIG. 5A). CBE11 elicits a similar effect with the Group III mAb CDH10 (FIG. 5B).

The cytotoxicity caused by administering a combination of anti-LT-β-R mAbs in solution is not peculiar to the HT29 tumor cell line. FIG. 5C shows that the Group I AGH1 mAb and the Group III CDH10 mAb act synergistically in killing two different tumor cell lines (HT29 cells and WiDr cells) derived from human adenocarcinoma tumors.

Summary of Anti-LT-β-R mAbs Characteristics

All of the anti-LT-β-R mAbs of this invention, when cross-linked by immobilization, act as LT-β-R activating agents in the presence of a second LT-β-R activating agent such as IFN-γ. The ability of anti-LT-β-R mAbs to act as LT-β-R activating agents in the presence or absence of LT-α1/β2 in solution often varies according to the state of the cells at the time of the test. Table 2, infra, summarizes the properties of the anti-LT-β-R mAbs characterized by this invention.

Figure 3B:
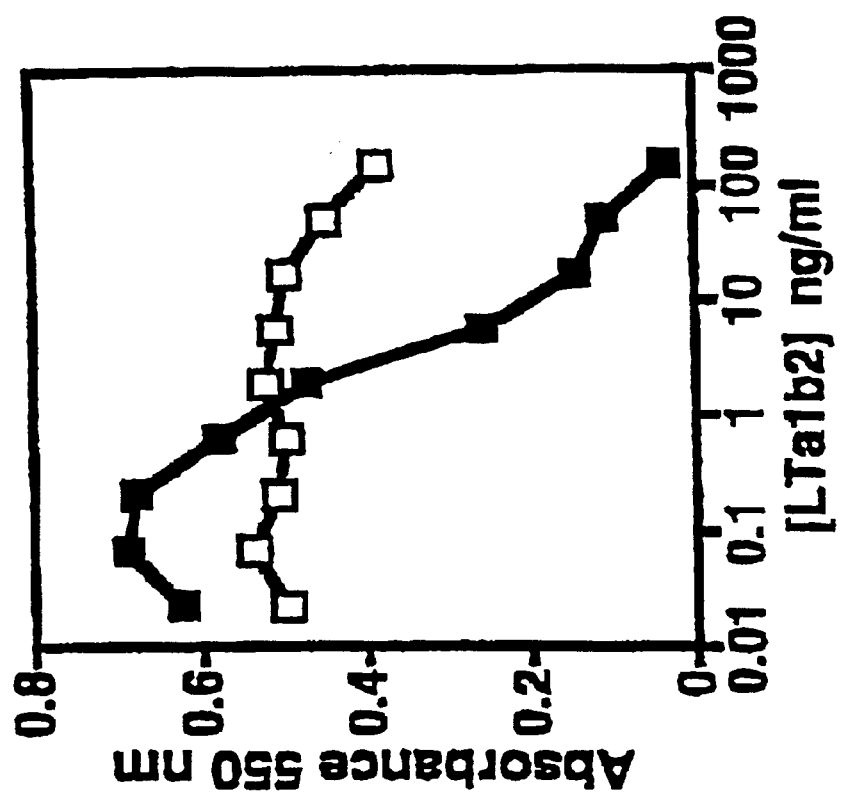

The Group I mAbs BDA8 and AGH1 do not function as LT-β-R activating agents in solution with LT-α1/β2. The BDA8 mAb actually blocks the anti-tumor effect of LT-α1/β2 (FIG. 3B and Table 2). In contrast, the Group II anti-LT-β-R mAbs BCG6 and BHA10 have mixed agonistic and antagonistic effects when administered with LT-α1/β2. The Group III anti-LT-β-R mAbs BKA11 and CDH10 are unique in their ability to act as LT-β-R activating agents which potentiate anti-tumor effects in the presence of LT-α1/β2 and a second LT-β-R activating agent such as IFN-γ without exhibiting the antagonistic effects often seen with the Group II mAbs BCG6 and BHA10.

It is important to keep in mind that the classification of the anti-LT-β-R mAbs based on their ability to cooperate in tumor cell cytolytic assays reflects that they interact with distinct epitopes of the LT-β-R. The mAbs comprising a single group do not, however, necessarily have the same binding affinities for their cognate epitopes. Thus the variable results seen when comparing the effects of different mAbs belonging to the same or different groups may represent differences in binding affinities. Accordingly, it is possible that a Group I or a Group IV mAb with a higher binding affinity for the LT-β-R could be isolated which would function like the Group III mAbs as a LT-β-R activating agent in the presence of LT-α1/β2.

The hybridoma cell lines or subclones thereof which produce the anti-LT-β-R mAbs described above were deposited on Jan. 12, 1995 with the American Type Culture Collection (ATCC) (10801 University Blvd (Manassas, Va.) according to the provisions of the Budapest Treaty, and were assigned the ATCC accession numbers designated as follows:

|   | CELL LINE   | mAb Name | ATCC Accession No. |
|---|-------------|----------|--------------------|
| a) | AG.H1.5.1  | AGH1     | HB 11796           |
| b) | BD.A8.AB9  | BDA8     | HB 11798           |
| c) | BC.G6.AF5  | BCG6     | HB 11794           |
| d) | BH.A10     | BHA10    | HB 11795           |
| e) | BK.A11.AC10| BKA11    | HB 11799           |
| f) | CB.E11.1   | CBE11    | HB 11793           |
| g) | CD.H10.1   | CDH10    | HB 11797           |

All restrictions on the availability to the public of the above ATCC deposits will be irrevocably removed upon the granting of a patent on this application.

Anti-LT-β-R IgM Monoclonal Antibodies Function as LT-β-R Activating Agents

Anti-LT-β-R mAbs which comprise more than the usual two IgG antigen binding sites will also function in solution as cell surface LT-β-R cross-linking agents, and will accordingly fall within the definition of a LT-β-R activating agent according to this invention. The antigen binding sites of an anti-LT-β-R mAb can be built into IgM molecules—which have ten antigen binding sites—using standard recombinant DNA and hybridoma techniques (Example 12).

Alternatively, one may collect and enrich for complete mouse (or other animal) IgM molecules isolated by hybridoma fusion techniques after a single immunization with antigen. One way to enrich for IgM molecules would be to immunize CD40 signaling-deficient mice (Kawabe et al., *Immunity*, 1, pp. 167–78 (1994); Xu et al., *Immunity*, 1, pp. 423–31 (1994)). These mice cannot effectively produce IgGs and therefore their response to challenge by antigen is enriched for IgM isotypes.

Anti-LT-β-R IgM antibodies, by virtue of their increased valency, can effectively aggregate LT-β-R molecules within the plane of the membrane, thereby enhancing LT-β-R signaling as compared to their IgG counterparts having two antigen binding sites. A dramatic example of the increased efficiency of multivalent antibodies in receptor clustering is seen with antibodies to the Fas receptor, where the IgM form is very potent and normal bivalent IgGs are not effective in solution (Yonihara and Yonihara, *J. Exp. Med.*, 169, pp. 1747–56 (1989); Alderson et al., *Int. Immunol.*, 6, pp. 1799–1806 (1994)).

Likewise, the apo-1 mAb to the Fas receptor is an IgG3 mAb. This mAb is a potent cytotoxic agent which relies on Fc interactions unique to IgG3 subtypes to aggregate into larger polyvalent forms. Removal of the Fc region creates a F(ab)$_2$ form that cannot associate into larger aggregates and which is inactive (Dhein et al., *J. Immunol.*, 149, pp. 3166–73 (1992)). Thus by analogy, it is predicted that IgM versions of anti-LT-β-R mAbs will be potent anti-tumor agents.

Anti-LT-β-R mAbs Inhibit Tumor Growth in Mice

The ability of a LT-β-R activating agent such as an anti-LT-β-R mAb to inhibit human tumor cell growth in vitro (Examples 6–8 and 13) may be indicative in vivo anti-tumorigenic activity. Experiments performed in immunodeficient (SCID) mice demonstrate that an anti-LT-β-R mAb (CBE11) can efficiently block tumor formation by human adenocarcinoma WiDr cells (Example 14; FIG. 6). Mice inoculated subcutaneously (s.c.) with WiDr cells form measurable tumors within two weeks. When mice were treated i.p. with the CBE11 mAb at the same time as the WiDr cells were inoculated s.c., tumor outgrowth was dramatically blocked (FIG. 6A). The anti-tumor action of the CBE11 anti-LT-β-R mAb was enhanced by adding IFN-γ; CBE11 was effective, however, even without exogenous IFN-γ. In the CBE11+IFN-γ group, 7 of 16 animals completely lacked tumors, whereas the remaining animals had small nodules that had not progressed at 2 months. The CBE11 alone treated mice were similar to the CBE11+IFN-γ group at 30 days. The CBE11 alone treated mice, however, eventually developed slowly growing tumors. There were statistically significant differences between the CBE11 (+/−IFN-γ) groups and the control groups (saline, IFN-γ alone and control anti-human LFA-3 mAb (1E6)+IFN-γ), but no significant differences among the control groups. The 1E6 and CBE11 mAbs are both IgG1 antibodies. The 1E6 mAb effectively coats the tumor cells but does not block tumor growth. Thus complement or natural killer cell-mediated events are not the sole basis for the anti-tumor activity of the CBE11 anti-LT-β-R mAb.

The efficacy of the CBE11 mAb in inhibiting tumor growth in vivo in the absence of exogenous IFN-γ was unexpected since there was dependence on IFN-γ for measurable LT-β-R-based in vitro cytotoxic effects. Either there is some crossover of mouse IFN-γ onto human IFN-γ receptors, or other mechanisms may be involved in vivo.

Figure 6B:
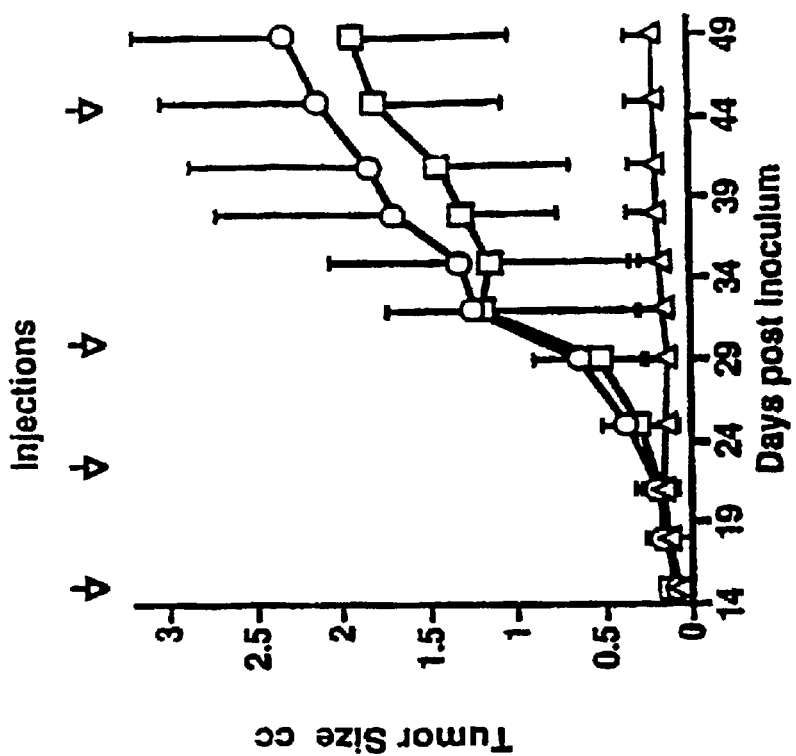
FIG. 6. Tumor size in SCID mice treated with an anti-LT-β-R mAb. (A) Size of the human adenocarcinoma WiDr tumor in SCID mice 30 days after inoculation with an antibody co-treatment. Mice were treated on days 1 and 2 with saline, IFN-γ alone, an anti-LT-β-R mAb (CBE11) with and without IFN-γ and a control anti-human LFA-3 mAb (1E6) with IFN-γ. The mean of each group is indicated by a crossbar. Means, standard deviations, and number of animals (in parentheticals) for the five groups (left to right) were: 0.88+/−0.59 (14), 1.21+/−0.7 (21), 0.041+/−0.052 (16), 0.11+/−0.1 (12), and 0.98+/−1.16 (12). (B) Size of the human adenocarcinoma WiDr tumor in SCID mice from 14 to 49 days after tumor cell inoculation with a 15 day post-inoculation antibody treatment. Tumors were grown to an average diameter of 0.53 cm (0.076 cc) without any treatment and i.p. injections were started on day 15 and continued as indicated by the arrows. Means and standard deviations are indicated for a group of 12 animals treated either with IFN-γ alone (1×10$^6$ U/injection) (-□-), IFN-γ with 50 μg 1E6 anti-LFA-3 mAb (-○-), IFN-γ with 50 g CBE11 anti-LT-β-R mAb (-Δ-) or 50 μg CBE11 anti-LT-β-R mAb alone (not shown).
Figure 6A:
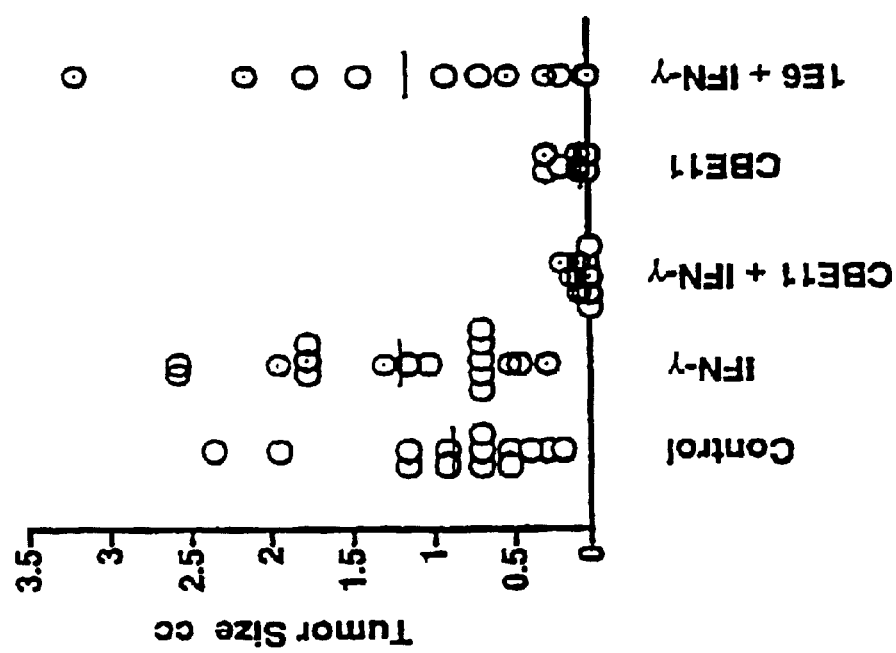

The CBE11 anti-LT-β-R mAb can also inhibit growth of an established tumor in mice (FIG. 6B). Mice were inoculated s.c. with WiDr human adenocarcinoma cells at day 1 and tumors were allowed to develop for 15 days (Example 14). Tumors in animals treated i.p. with IFN-γ alone, or with the control anti-human LFA-3 mAb (1E6)+IFN-γ, continued to increase in size over the course of the 7-week experiment. In contrast, tumors treated with the CBE11 anti-LT-β-R mAb (+IFN-γ or alone) stopped growing, and following three injections of CBE11 antibody over a three week period, tumor growth was arrested out to 49 days post-inoculum when the experiment was terminated (FIG. 6B).

These experiments demonstrate that an anti-LT-β-R mAb which activates LT-β-R signaling can effectively inhibit tumor formation at early stages and can also block continued tumor cell growth at later stages of tumorigenesis in vivo. These experiments also demonstrate that administration of a single LT-β-R activating agent may be effective for treating or reducing the advancement, severity or effects of neoplasia in an affected animal.

The procedures described in Example 14 may be used to identify LT-β-R activating agents according to this invention which function alone or in combination to inhibit tumor cell growth in vivo. It is envisioned that other LT-β-R activating agents—including but not limited to those identified using in vitro tumor cell cytotoxicity assays—may have similar anti-tumor effects in vivo when administered either alone or in combination to animals or humans.

The Use of IFN-γ and Other LT-β-R Activating Agents

The cytotoxic effects of LT-α/β heteromeric complexes and of cross-linked or multiple anti-LT-β-R Abs on tumor cells is enhanced by the presence of a LT-β-R activating agent, particularly IFN-γ. Human adenocarcinoma cells of intestinal origin (HT29 cells) have previously been shown to be sensitive to FasR signaling (Yonehara and Yonehara, *J. Exp. Med.*, 169, pp. 1747–56 (1989)); and to TNF and LT-α in the presence of IFN-γ (Browning et al., *J. Immunol.*, 143, pp. 1859–67 (1989)).

The amount of LT-β-R activating agent required to enhance the anti-tumor activity of LT-α/β heteromeric complexes, anti-LT-β-R Abs or other LT-β-R activating agents of this invention will depend on the cell or tissue type being treated, and also with the mode of treatment, and can be determined empirically using routine procedures. The LT-β-R activating agent can be provided at a concentration or delivered at a rate determined to be effective in conjunction with other LT-β-R activating agents administered, taking into consideration the factors listed above.

Alternatively, endogenous LT-β-R activating agents such as interferons like IFN-γ, which may be produced by cells or tissue surrounding the target tumor cells, can be relied upon. Endogenous IFN-γ is normally produced upon viral infection, and is also found in the vicinity of tumors (Dinge et al., *Immunity*, 1, pp. 447–56 (1994)).

Any agent which is capable of inducing interferons, preferably IFN-γ, and which potentiates the cytotoxic effects of LT-α/β heteromeric complexes and anti-LT-β-R mAbs on tumor cells falls within the group of LT-β-R activating agents of this invention. While virus infection normally induces IFN-γ production, the levels of endogenous IFN-γ may be enhanced by other agents (Example 10). For example, clinical experiments have demonstrated interferon induction by double stranded RNA (dsRNA) treatment. Accordingly, polyriboguanylic/polyribocytidylic acid (poly-rG/rC) and other forms of dsRNA are effective as interferon inducers (Juraskova et al., *Eur. J. Pharmacol.*, 221, pp. 107–11 (1992)).

The interferon stimulator from Glycyrrhiza glabra (Acharya et al., *Indian J. Med. Res.*, 98, pp. 69–74 (1993)), and pharmaceutical agents, many of which are orally administrable, may also be used to boost endogenous interferon levels. Such interferon inducers include: imiquimod (Bernstein et al., *Antiviral Res.*, 20, pp. 45–55 (1994)); saparal (Paramonova et al., *Vopr. Virusol.*, 39, pp. 131–34 (1994); aryl pyrimidones such as bropirimine (Onishi and Machida, *Hinyokika Kiyo*, 40, pp. 195–200 (1994)); Ridostin (Cheknev et al., *Vopr. Virusol.*, 39, pp. 125–28 (1994)).

Several of these interferon inducing agents have been characterized as inducers of type I interferons such as IFN-α. Type I interferons can also function as LT-β-R activating agents but are less potent than IFN-γ.

Treatments Using LT-α/β Complexes and LT-β-R Activating Agents

The compositions of this invention will be administered at an effective dose to treat the particular clinical condition addressed. Determination of a preferred pharmaceutical formulation and a therapeutically efficient dose regiment for a given application is well within the skill of the art taking into consideration, for example, the condition and weight of the patient, the extent of desired treatment and the tolerance of the patient for the treatment.

Typically, humans can tolerate up to 100–200 $\mu g/m^2$ of TNF before serious toxicity is manifested (Schiller et al., Cancer Res., 51, pp. 1651–58 (1991)). In mice, dosages in the range of 1–5 $\mu g$/mouse/day given with $5 \times 10^4$ units of recombinant human IFN-$\gamma$ caused human primary tumor regression (Balkwill et al., CIBA Foundation Symposium (1987); Havell et al., J. Exp. Med., 167, pp. 1067–85 (1988)). Based on the relative effectiveness of TNF and LT-$\alpha 1/\beta 2$ in the HT29 cytolytic assays, approximately 5–25 $\mu g$/mouse/day of LT-$\alpha 1/\beta 2$ will provide a therapeutic dose range. Extrapolating to the human, it is expected that LT-$\alpha 1/\beta 2$ dosages of at least 1 $mg/m^2$ will be required in combination with an LT-$\beta$-R activating agent such as IFN-$\gamma$.

Historically, IFN-$\gamma$ therapy has been undertaken either at maximum tolerated doses in the range of 100–250 $\mu g/m^2$, or at "immunomodulatory" levels in the range of 10–25 $\mu g/m^2$ (see e.g. Kopp et al., J. Immunother., 13, pp. 181–90 (1993)). Combination therapies with two interferons have used $4 \times 10^6$ units/$m^2$ of IFN-$\alpha$ and approximately 250 $\mu g/m^2$ of IFN-$\gamma$ (Niederle et al., Leuk. Lymphoma, 9, pp. 111–19 (1993)). Intermediate doses of about 25–100 $\mu g/m^2$ of IFN-$\gamma$ in combination with the LT-$\alpha/\beta$ heteromeric complexes or purified anti-LT-$\beta$-R-Abs described herein are expected to be suitable starting points for optimizing treatment doses.

Administration of the LT-$\alpha/\beta$ heteromeric complexes and cross-linked anti-LT-$\beta$-R Abs of this invention, including isolated and purified forms of the antibodies or complexes, their salts or pharmaceutically acceptable derivatives thereof, may be accomplished using any of the conventionally accepted modes of administration of agents which exhibit anti-tumor activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application. Modes of administration may include oral, parenteral, subcutaneous, intravenous, intralesional or topical administration.

The LT-$\alpha/\beta$ heteromeric complexes, IFN-$\gamma$, and anti-LT-$\beta$-R Abs may, for example, be placed into sterile, isotonic formulations with or without cofactors which stimulate uptake or stability. The formulation is preferably liquid, or may be lyophilized powder. For example, the LT complexes and/or anti-LT-$\beta$-R Abs and IFN-$\gamma$ may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., Biopolymers, 22, pp. 547–56 (1985)); poly(2-hydroxyethyl-methacrylate) or ethylene vinyl acetate (Langer et al., J. Biomed. Mater. Res., 15, pp. 167–277 (1981); Langer, Chem. Tech., 12, pp. 98–105 (1982)).

Liposomes containing LT-$\alpha/\beta$ heteromeric complexes and/or anti-LT-$\beta$-R Abs and IFN-$\gamma$ can be prepared by well-known methods (See, e.g. DE 3,218,121; Epstein et al., Proc. Natl. Acad. Sci. U.S.A., 82, pp. 3688–92 (1985); Hwang et al., Proc. Natl. Acad. Sci. U.S.A., 77, pp. 4030–34 (1980); U.S. Pat. Nos. 4,485,045 and 4,544,545). Ordinarily the liposomes are of the small (about 200–800 Angstroms) unilamellar type in which the lipid content is greater than about 30 mol. % cholesterol. The proportion of cholesterol is selected to control the optimal rate of LT complex and/or anti-LT-$\beta$-R Abs and IFN-$\gamma$ release.

The LT-$\alpha/\beta$ heteromeric complexes and anti-LT-$\beta$-R Abs of this invention may also be attached to liposomes containing other LT-$\beta$-R activating agents, chemotherapeutic agents or IFN-$\gamma$ to supplement the IFN-$\gamma$ typically found in the region of tumors. Attachment of LT complexes and anti-LT-$\beta$-R Abs to liposomes may be accomplished by any known cross-linking agent such as heterobifunctional cross-linking agents that have been widely used to couple toxins or chemotherapeutic agents to antibodies for targeted delivery. Conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

Advantages of therapeutic compositions based on anti-LT-$\beta$-R activation

An anti-tumor therapy based upon LT-$\beta$-R activation would have several advantages. LT-$\beta$-R binds to LT-$\alpha/\beta$ heteromeric complexes with high affinity in $\beta/\beta$ clefts, and with lower affinity in $\alpha/\beta$ clefts created at the interfaces between adjacent LT-$\alpha$ and LT-$\beta$ subunits. In contrast, the TNF receptors bind to LT-$\alpha/\beta$ heteromeric complexes with high affinity only in $\alpha/\alpha$ clefts. Accordingly, purified LT-$\alpha 1/\beta 2$ complexes bind with high affinity to LT-$\beta$-R between adjacent LT-$\beta$ subunits, but lack $\alpha/\alpha$ clefts and thus do not cross-activate signaling through the TNF receptors. Thus the LT-$\alpha/\beta$ heteromeric complexes of this invention will not stimulate TNF-associated inflammatory responses.

LT-$\alpha 1/\beta 2$ administration does not activate endothelial cell changes associated with inflammatory response even at relatively high levels. For this reason, the side effects due to activation of the inflammatory cascades observed with TNF should not be a problem using the pharmaceutical compositions and treatment methods to activate the LT-$\beta$-R.

Human LT-$\alpha 1/\beta 2$ binds to mouse LT-$\beta$-R essentially as well as to human LT-$\beta$-R. Injection of 100 $\mu g$ human LT-$\alpha 1/\beta 2$ per mouse is not lethal (Example 11), suggesting that stimulation of LT-$\beta$-R in the whole animal does not have the overt toxicity seen when similar experiments were tried with FasR or p60 TNF-R activation.

The use of specific anti-LT-$\beta$-R monoclonal antibodies or antibody combinations to trigger this pathway in humans may have several advantages over treatment with LT-$\alpha/\beta$ heteromeric complexes. An anti-receptor antibody therapy will be more selective than treating with ligand. Moreover, recombinant forms of anti-LT-β-R mAbs would be easier to engineer and produce in large scale than the soluble LT-α/β heteromeric complexes.

It is envisioned that the mAbs or LT-α/β heteromeric complexes would be administered to tumor-bearing people in conjunction with a conventional anti-tumor therapy (i.e. radiation and chemotherapy). A combined treatment of LT-β-R activation with conventional chemotherapies may provide an extra factor of tumor killing activity that would be more likely to clear a patient of tumorigenic cells than when conventional anti-tumor therapy is used alone.

It is further possible that this approach may have relatively few side effects and therefore could be given in a semi-prophylactic sense in cases of carcinomas that may not have metastasized, or in patients from families who show a genetic pre-disposition for a certain type of cancer.

The following are examples which illustrate the LT-α/β heteromeric complexes and the anti-LT-β-R mAbs of this invention and the methods used to characterize them. These examples should not be construed as limiting: the examples are included for purposes of illustration and the present invention is limited only by the claims.

EXAMPLE 1

Generation of Baculovirus-infected Insect Cell Supernatants Containing LT-α/β Forms Recombinant baculovirus encoding either full length LT-α or a secreted form of LT-β were made as described (Crowe et al., *Science*, 264, pp. 707-710 (1994)). High five insect cells (Invitrogen, San Diego, Calif.) were inoculated at a density of $2 \times 10^5$ cells/ml into 7.2 liters of SF 900-II (Bibco media without serum. The culture reached $1.8 \times 10^6$ cells/ml 48 hours later and was infected with 150 ml ($3 \times 10^8$ PFU/ml) of LT-β and 300 ml of LT-α baculovirus stocks. Two days later, the culture was harvested and the cell debris was removed by centrifugation. After addition of EDTA and PMSF (1 Mm EDTA and 150 μM PMSF final concentration), the clarified supernatant was concentrated 10-fold by ultrafiltration using a S1YM10 (Amicon) spiral cartridge. The concentrate was divided into six 120 ml portions and aliquots were stored at −70 C prior to purification.

EXAMPLE 2

Preparation of Soluble LT-β Receptors as Immunoglobulin Fc Chimera

The extracellular domain of LT-β-R up to the transmembrane region was amplified by PCR from a cDNA clone using primers that incorporated NotI and SalI restriction enzyme sites on the 5' and 3' ends, respectively (Browning et al., *J. Immunol.*, 154, pp. 33–46 (1995)). The amplified product was cut with NotI and SalI, purified and ligated into NotI-linearized vector pMDR901 along with a SalI-NotI fragment encoding the Fc region of human IgG1. The resultant vector contained the dihydrofolate reductase gene and the LT-β-R-Fc chimera driven by separate promoters. The vector was electroporated into CHO dhfr⁻ cells and methotrexate-resistant clones were isolated as per standard procedures. The LT-β-R-Fc is secreted into the medium and an ELISA assay was used to select for cell lines producing the highest level of the chimeric protein. A high-producing cell line was grown to large numbers and conditioned medium collected. The pure protein was isolated by Protein A sepharose fast flow affinity chromatography.

EXAMPLE 3

Affinity Purification of LT-α1/β2 Using TNF-R and LT-β-R

To prepare resins for the receptor affinity purification of LT forms, purified preparations of LT-β-R-Fc (as described in Example 2 herein) and TNF-R p60-Fc (Crowe et al., *Science*, 264, pp. 707–10 (1994)) were immobilized on CNBr-sepharose (Pharmacia) at 5 mg/ml resin essentially following the manufacturer's specifications. The resins were put through one elution cycle prior to use. A portion (120 ml) of the S1Y10 concentrate was passed over two sequential p60 TNF-R-Fc columns, which bind LT-α and LT-α2/β1. The flow through, which contained LT-α1/β2 and LT-β, was passed over a LT-β-R-Fc column. The column was washed with 5 volumes each of PBS, PBS with 0.5 M NaCl and PBS, and then the LT-α and LT-α2/β1 complexes were eluted with 25 mM sodium phosphate, 100 mM NaCl, pH 3.5. Elution fractions were immediately neutralized with 1/20 volume of 0.5 M sodium phosphate, pH 8.6 and stored on ice. Fractions containing protein were identified by absorbance at 280 nm, peak fractions were pooled and the elution pools from the columns were analyzed by SDS-PAGE stained with coomassie brilliant blue. Elution as described above yielded greater than 95% pure LT-α1/β2.

EXAMPLE 4

Characterization of the Purified LT-α1/β2 Ligands

The fractions of Example 3 were sized by gel exclusion chromatography to assess whether trimers were formed and if aggregates were present. A TSK G3000 sw x2 column was used at a flow rate of 0.5 ml/min to size separate a BioRad gel filtration protein standard, and the three different LT trimers, LT-α3, LT-α2/β1 and LTα1/β2. FIG. 1A shows that very little, if any, of the LT-α1/β2 trimers show up as high molecular weight aggregate. Comparison to size standards shows that the three forms are all trimeric, i.e. about 50–60 kDA. Assuming the trimer, the stoichiometry of LT-α to LT-β contained in the purified LT-α1/β2 and LT-α2/β1 fractions was evaluated by either densitometry of the coomassie stained gels or by peak height analysis of the two peaks following resolution on C4 reverse phase HPLC. Both measurements confirmed the identity of the fractions eluted off the affinity columns as described above.

Figure 1B:
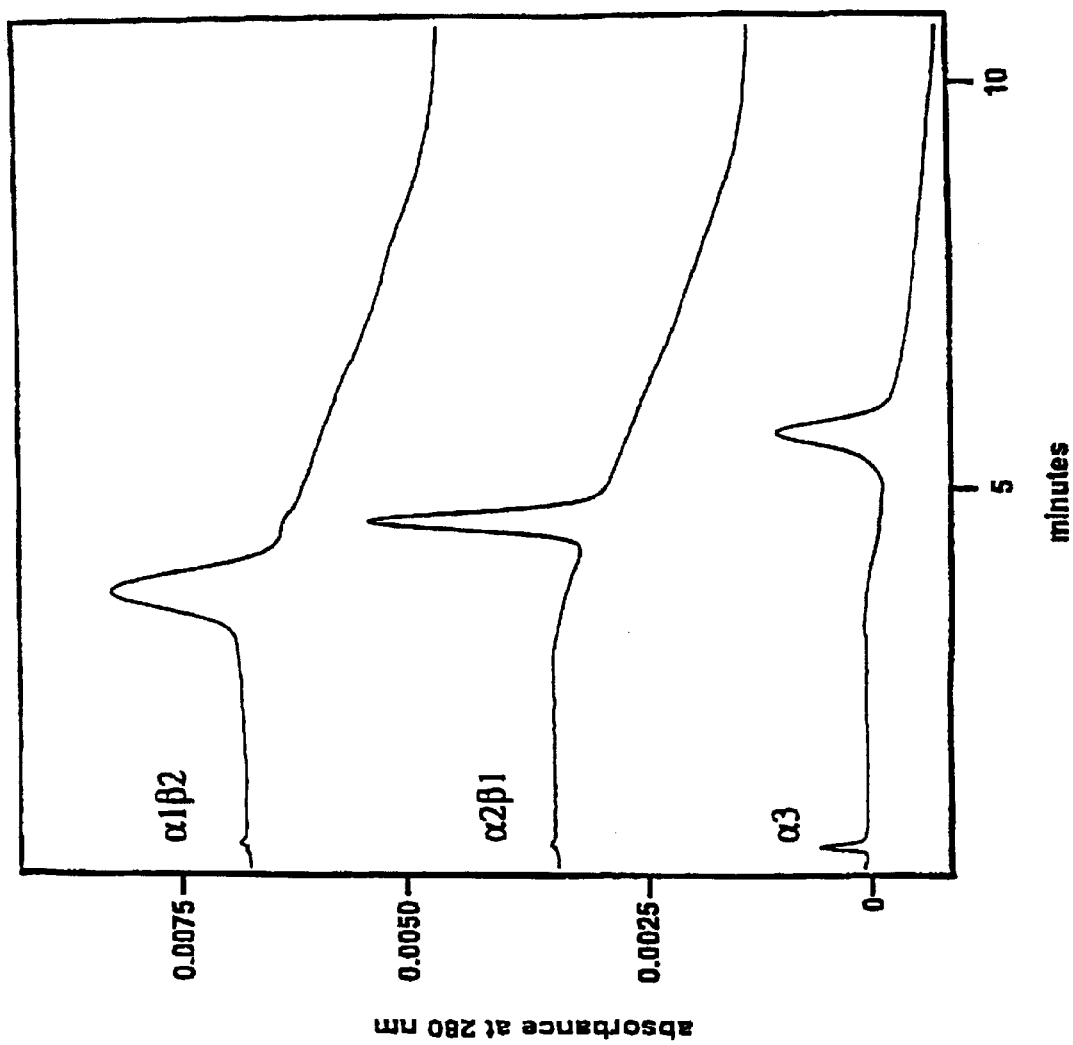
FIG. 1B. Ion exchange analyses of purified LT forms using a Poros carboxymethyl column (4.6 mm×100 mm) on a BioCad instrument (Perceptive Biosystems). 27 μg of each sample protein was loaded onto a column and eluted in a gradient of 0 to 1M NaCl over 20 column volumes at 5 ml/min in a Buffer containing 16.66 μM Hepes, 16.66 μM Na Acetate, and 16.66 μM Mes buffer (pH 6.5).

The purity of the preparations was further assessed by ion exchange chromatography using BioCAD instrumentation to run pH maps of LT-α1/β2 and LT-α2/β1 on the weak cation exchanging resin under several different buffer systems. The method that exhibited the greatest ability to cleanly retain and separate the three trimers incorporated a POROS CM (carboxymethyl) column run at 5 ml/min with a 16.66 mM MES, 16.66 mM HEPES, 16.66 mM Na Acetate pH 6.5 buffer and eluting with a 1 M NaCl gradient over 20 column volumes. The BioCAD chromatograms of LT-α1/β2 and LT-α2/β1 complexes are shown in FIG. 1B. Each trimer, LT-α3, LT-α2/β1 and LT-α1/β2 eluted at a different salt concentration and there was no evidence for cross contamination of more than 1–2% in the various preparations.

EXAMPLE 5

Killing of HT29 Human Adenocarcinoma Cells by Soluble LT-α1/β2 Complexes

The HT29 cytolytic assay has been previously described (Browning and Ribolini, *J. Immunol.*, 143, pp. 1859–67

(1989)). In a typical assay, serial dilutions of LT-α1/β2 (and other cytokines where applicable) were prepared in 0.05 ml in 96 well plates and 5000 trypsinized HT29-14 cells added in 0.05 ml of media containing 0 or 80 U/ml (anti-viral units) of human IFN-γ. HT29-14 cells are from a subclone of the original ATCC-derived HT29 line that is more homogeneous. HT29-14 cells were used in the assays; all of these results can also be observed using the original ATCC-derived HT29 line. After 3–4 days, mitochondrial reduction of the dye MTT was measured as follows: 10 l of MTT was added and after 3 hours, the reduced dye dissolved with 0.09 ml of isopropanol with 10 mM HCl, and the O.D. measured at 550 nm. Soluble receptor forms prepared as described herein, or pure human IgG were added in 10 μl prior to the cells to give a final concentration of 5 μg/ml.

Figures 2, 2A:
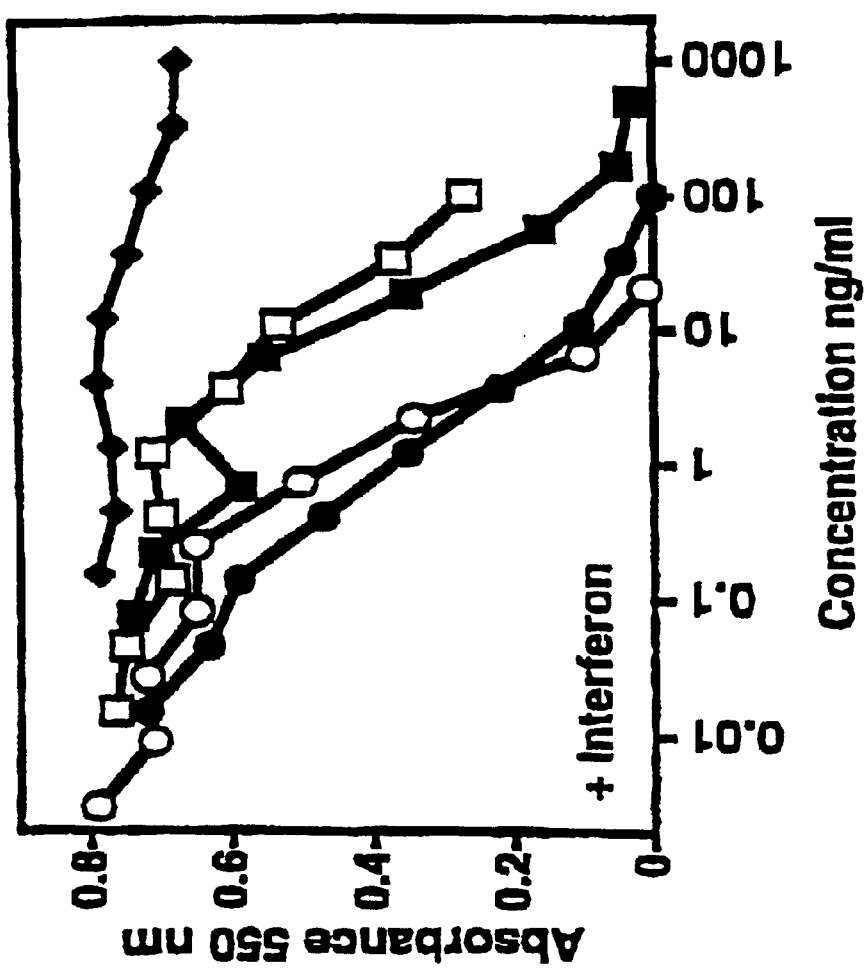
FIG. 2A. Comparison of the cytotoxic activity of: Anti-Fas receptor mAb CH-11 (-●-); TNF (-○-); LT-α (-□-); LT-α1/β2 (-■-); and LT-α2/β1 (-◆-) on human adenocarcinoma HT29 cells in either the presence or absence of 80 U/ml IFN-γ.
Figures 1, 2A:
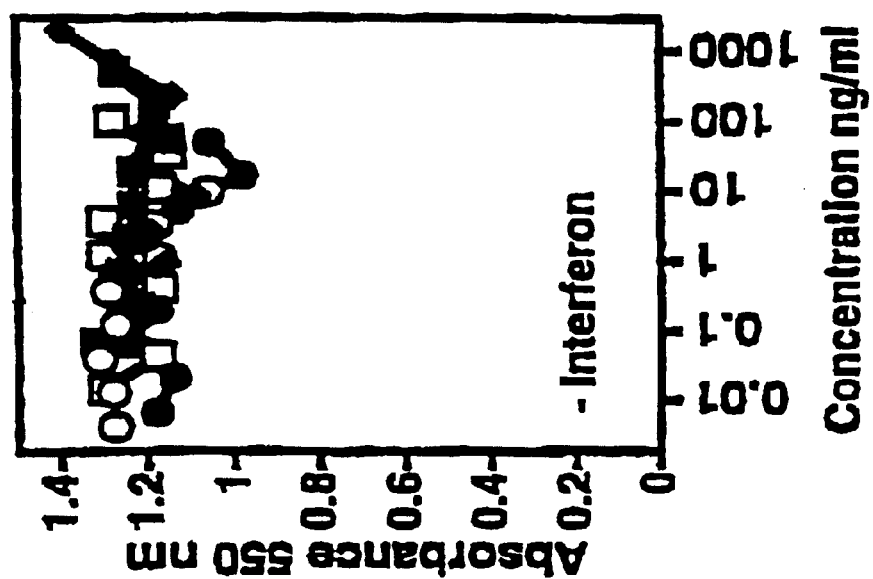

FIG. 2A shows the killing of HT29 cells by treating with anti-Fas receptor mAb CH-11 (which stimulates FasR signaling); TNF, LT-α3, LT-α1/β2 and LT-α2/β1 ligands in conjunction with IFN-γ. Visual inspection of the cells treated with LT-α1/β2 reveals that this agent kills cells rather than just blocking cell proliferation. In the absence of IFN-γ, no effects are observed, reflecting the unusual ability of IFN-γ to influence how cells interpret signaling from the TNF family of receptors. Interferons α and β were 100-fold less effective than IFN-γ as quantitated based on anti-viral activity units.

Figures 1, 2B:
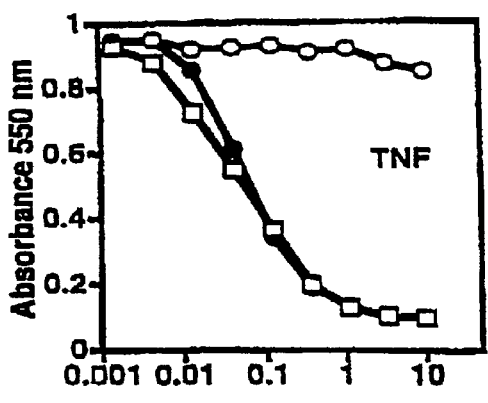
FIG. 2B. Comparison of the ability of 5 μg/ml of human IgG (-●-), soluble p60TNF-R-Fc (-○-) and soluble LT-β-R-Fc receptor-immunoglobulin chimeras (-□-) to inhibit the cytotoxic effects in FIG. 2A in the presence of 80 U/ml IFN-γ.
Figures 2, 2B:
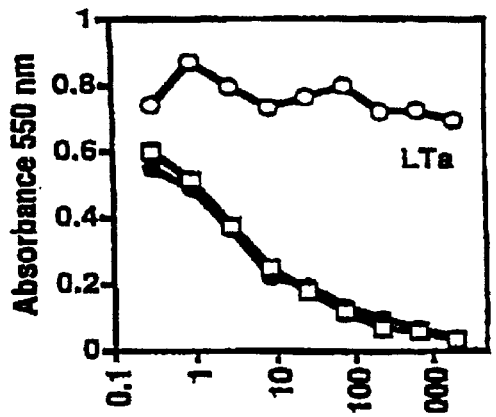

FIG. 2B shows the inhibition of LT-α1/β2 killing by soluble LT-β-R-Fc but not p60-TNF-R-Fc, demonstrating that cytotoxicity is specific to LT-α1/β2. The lack of inhibition by p60-TNF-R-Fc indicates that contaminating LT-α (known to be less than 1%) cannot account for the cytotoxic activity of LT-α1/β2.

EXAMPLE 6

Anti-LT-β-R mAbs Potentiate the Killing of HT29 Cells by LT-α1/β2 Complexes

Figures 2, 2B, 3:
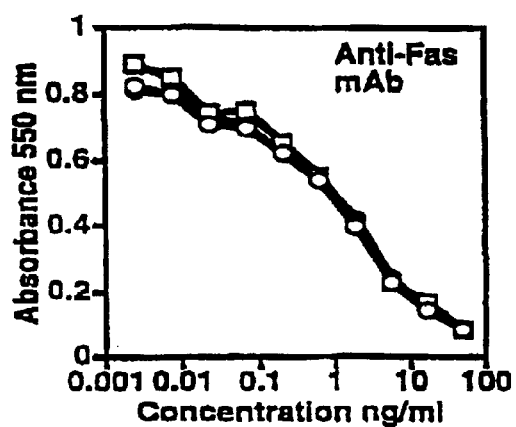
FIG. 3. Anti-LT-β-R mAbs potentiate the cytotoxic effect of LT-α1/β2 on human adenocarcinoma HT29 cells. (A) The LT-α1/β2 cytolytic effects on HT29 cells are potentiated by the presence of anti-LT-β-R mAb CDH10. LT-α1/β2 effects were measured without mAb (-●-), and in the presence of 0.5 μg/ml control IgG1 (-■-), 0.05 μg/ml CDH10 (-○-) and 0.5 μg/ml (-□-) CDH10. (B) The LT-α1/β2 cytolytic effects on HT29 cells are inhibited by the presence of the anti-LT-β-R mAb BDA8. LT-β1/β2 effects were measured in the presence of 2 μg/ml control IgG1 (-■-) or anti-LT-β-R mAb BDA8 (-□-). The difference between the behavior of the CDH10 and BDA8 anti-LT-β-R mAbs in this assay is one indication that they are directed to different epitopes of the LT-β-R.
Figures 2, 2B, 3, 4:
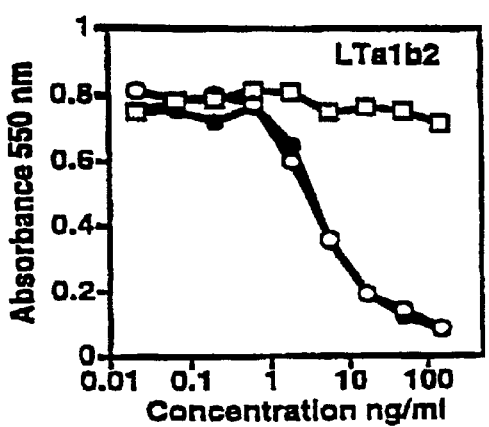
FIG. 4. Immobilized anti-LT-β-R mAbs are cytotoxic to human adenocarcinoma HT29 cells. (A) The anti-LT-β-R mAbs have a direct cytotoxic effect on HT29 cells when they are immobilized on a surface. Plates were coated with IgG1(-●-), a mAb directed against an unrelated abundant cell surface antigen HT29/26 (-■-), BDA8 (-○-) and CDH10 (-□-). (B) The effects of soluble anti-LT-β-R mAbs alone on the growth of HT29 cells. Symbols as in (A). These anti-LT-β-R mAbs in their soluble form do not have significant cytotoxic effects on HT29 cells when administered individually.
Figure 3A:
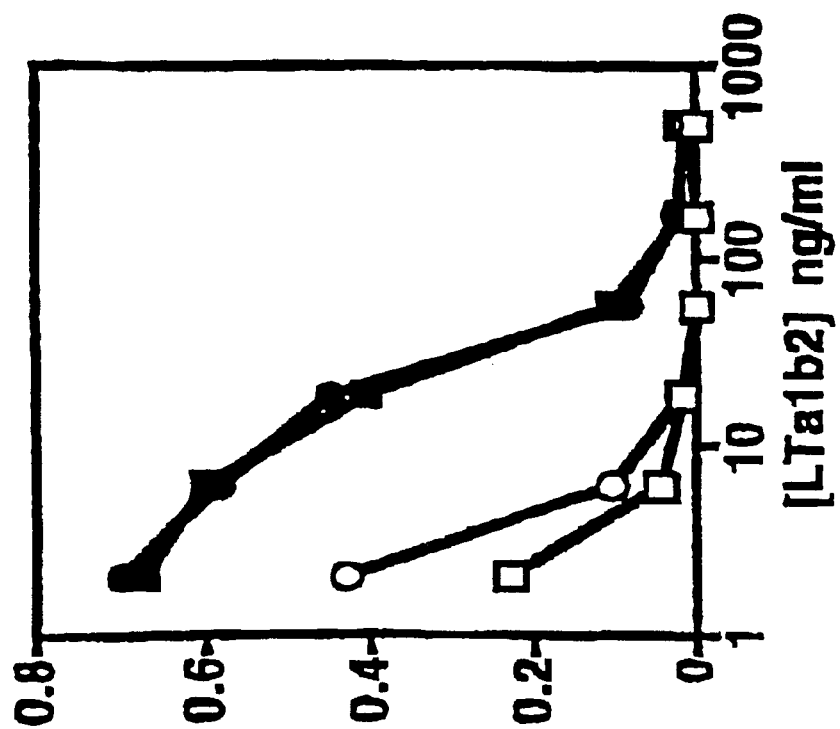

Cytolytic assays were performed as described in Example 5, except that IFN-γ and anti-LT-β-R mAbs (0.01–1000 ng/ml series) were added to the cells at 2× final concentration and then 50 μl of the cell solution were added to the wells containing diluted LT-α1/β2. Growth was assessed as described in Example 5. FIG. 3 shows the differential effects of two different anti-LT-β-R mAbs in their ability to potentiate LT-α1/β2 cytotoxic activity. FIG. 3A shows that the anti-LT-β-R mAb CDH10 potentiates LT-α1/β2 cytotoxic activity in a dosage-dependent manner. FIG. 3B shows the effects of another anti-LT-β-R mAb, BDA8, in the same assay. The BDA8 mAb inhibits the cytotoxic activity of LT-α1/β2 rather than potentiating tumor cell death.

EXAMPLE 7

Immobilized Anti-LT-β-R mAbs Can Kill HT29 Tumor Cells

Figure 4B:
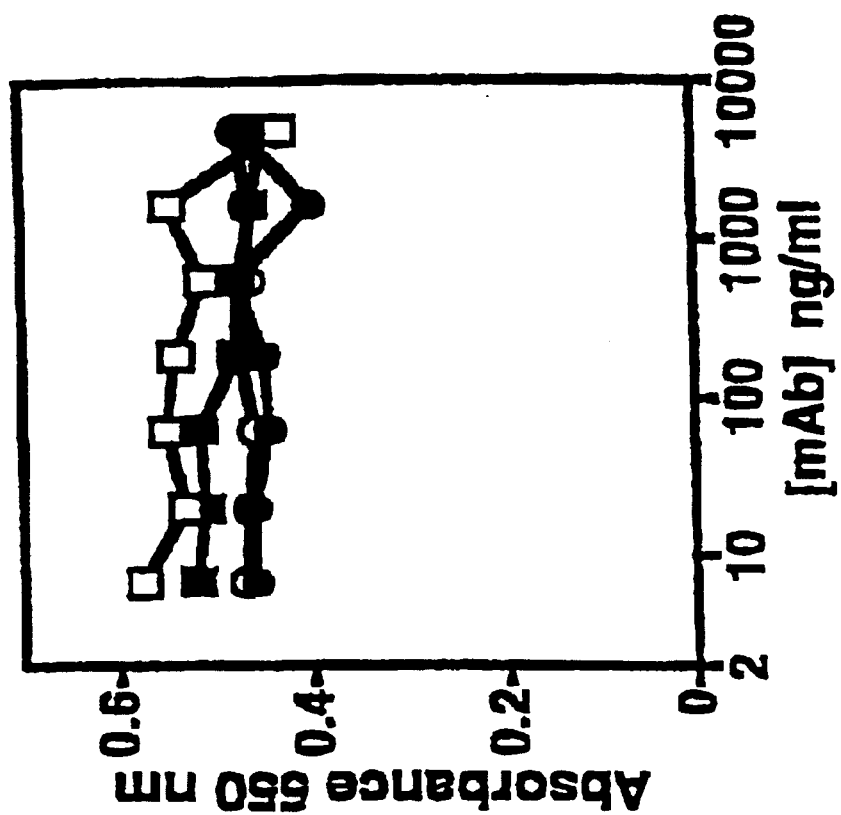
Figure 4A:
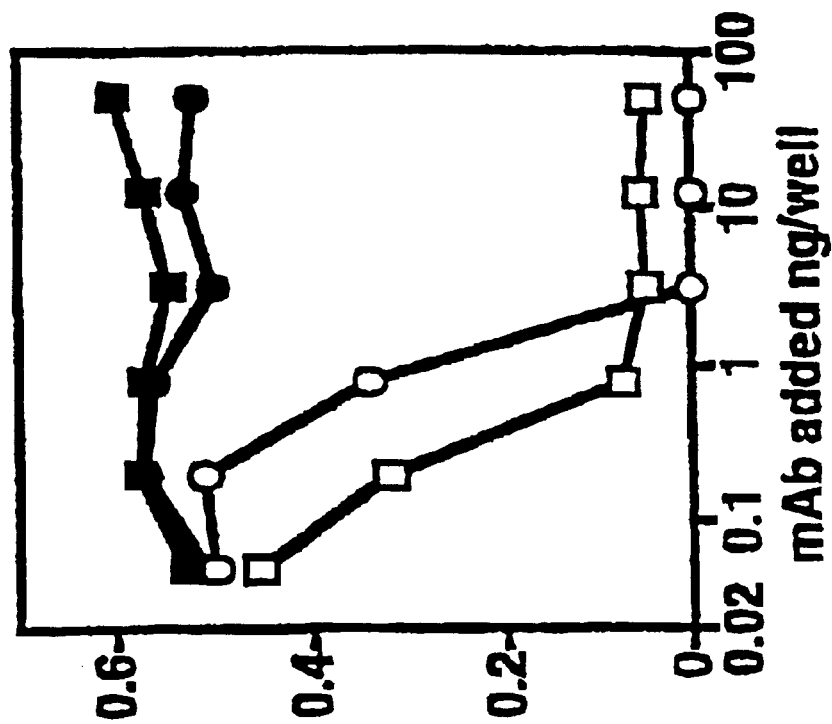

To immobilize anti-LT-β-R mAbs onto a plastic surface, 96-well tissue culture plates were coated with 50 μl of 10 μg/ml goat anti-mouse Fc polyclonal antibody (Jackson ImmunoResearch), washed and blocked with 5% FCS in PBS, followed by capture of the indicated anti-LT-β-R mAb and another wash. HT29 cells were plated into the mAb-coated wells, and cytolytic assays were conducted as in Example 5. FIG. 4A illustrates the cytotoxic effects of immobilized BDA8 and CDH10 anti-LT-β-R mAbs on HT29 cells. Each mAb individually elicits cytotoxicity on tumor cells when it is immobilized onto a surface. FIG. 4B shows that the same BDA8 and CDH10 anti-LT-β-R mAbs tested individually in solution are not cytotoxic and thus the cytolytic activity of a single anti-LT-β-R mAb in vitro appears to be a function of its immobilization.

EXAMPLE 8

A Combination of Anti-LT-β-R mAbs in Solution Directed Against Distinct Epitopes Kill HT29 Cells Growth of HT29 cells was assessed as described in Example 5 except that either one or two anti-LT-β-R mAbs were included in the growth medium. Table 1 shows the effects on HT29 cells observed when various anti-LT-β-R mAbs were included in solution (i.e., not immobilized on plastic). The anti-LT-β-R mAbs can be arranged into groups I–IV based on their relative abilities to work in combination with each other in a HT29 cytolytic assay. The anti-LT-β-R mAbs results generated in cytolytic assays parallel receptor binding data which suggest that the mAbs in each different group recognize different epitopes of the LT-β-R.

TABLE 1

Combinations of soluble anti-LT-β-R mAbs are cytotoxic to human adenocarcinoma HT29 cells. Anti-LT-β-R mAbs are grouped into Groups I, II, III and IV based on their effects in combination with each other in HT29 cell cytolytic assays. Pluses refer to the relative level of cytolytic effects of the mAb combination on HT29 cells in the presence of 80 U/ml IFN-γ.

| | | Second mAb | | | | | | |
|---|---|---|---|---|---|---|---|---|
| | First | Group I | | Group II | | Group III | | Group IV |
| Group | mAb | BDA8 | AGH1 | BCG6 | BHA10 | BKA11 | CDH10 | CBE11 |
| I | BDA8 | nr | – | + | ++ | + | nd | nd |
| | AGH1 | – | nr | ++ | +++ | ++ | nd | nd |
| II | BCG6 | ++ | ++ | nr | – | +++ | nd | nd |
| | BHA10 | ++ | +++ | – | nr | + | +++ | ++++ |
| III | BKA11 | + | ++ | +++ | nd | nr | – | nd |
| | CDH10 | ++ | ++ | ++ | +++ | – | nr | +++ |
| IV | CBE11 | nd | + | + | ++++ | nd | ++++ | nr | nr = not relevant; nd = not determined.

Figure 5D:
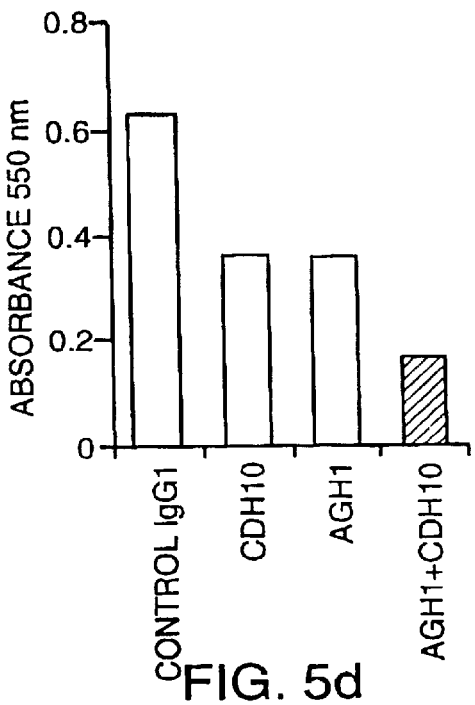

FIGS. 5A–D quantitates the effects of including in the HT29 cytolytic assay representative pairwise combinations of cooperating anti-LT-β-R mAbs directed against different epitopes of LT-β-R. FIG. 5A shows the cytotoxic effects of BHA10 and CBE11, FIG. 5B of CDH10 and CBE11, and FIG. 5C of CDH10 and AGH1, alone and in combination. FIG. 5D shows the cytotoxic effects of the CDH10 and AGH1 mAb combination in a different tumor cell line called WiDr.

Table 2 summarizes the characteristics of the representative anti-LT-β-R mAbs of this invention.

TABLE 2

Summary of Mouse Anti-human LT-β-R mAbs HT29 Cytotoxicity

| mAb Group | mAb Name | Cell Staining[a] | Blocking Receptor Binding[b] | mAb Immobilized on Plastic[c] | Soluble mAb alone | Soluble mAb with Ltα1β1 |
|---|---|---|---|---|---|---|
| I | BDA8 | +++ | +++ | + | +/−[d] | inhibits |
| I | AGH1 | +++ | +++ | + | +/− | inhibits |
| II | BCG6 | +++ | ++ | + | +/− | mixed |
| II | BHA10 | +++ | +++ | + | +/− | mixed |
| III | BKA11 | +++ | +/− | + | − | potentiates |
| III | CDH10 | +++ | +/− | + | +/− | potentiates |
| IV | CBE11 | +++ | +++ | + | +/− | no effect |
| Controls | MOPC21 | − | − | − | − | no effect |
| | HT29/26 | − | nd | − | − | no effect |
| | TS 2/9[e] | nd | nd | − | − | no effect |

[a]FACS staining of CHO cells transfected with the LT-β-R.
[b]Assay assessed whether antibody blocks binding of soluble receptor to the activated T-cell hybridoma II-23. nd = not done.
[c]HT-29 cells were grown with IFN-γ on anti-LT-β-R coated plates as defined in the methods.
[d]Variable, partial inhibition in some assays, no effects in others.
[e]Anti-human LFA-3, a mouse IgG1.

EXAMPLE 9

Reliance on Endogenous IFN-γ For the Treatment of Tumor Cells

IFN-γ, a preferred LT-β-R activating agent of the present invention, is a cytokine which exhibits anti-tumor activity and which is tolerated in humans. Endogenous IFN-γ present in the environment surrounding a tumor may be at sufficiently high concentrations to function as a LT-β-R activating agent of this invention without adding exogenous IFN-γ. The concentration of IFN-γ in the vicinity of a tumor may be ascertained using standard immunochemical techniques with tissue samples from the region of the tumor. If the endogenous concentration of IFN-γ is high enough to elicit anti-tumor activity in combination with the LT-α/β heteromeric complexes or anti-LT-β-R mAbs of this invention (as determined by the cytolytic assays described herein), then IFN-γ need not be administered as a second LT-β-R activating agent in the compositions or methods of this invention.

EXAMPLE 10

Induction of Endogenous IFN-γ as a LT-β-R Activating Agent for the Treatment of Tumor Cells Compounds which can induce the endogenous production of interferons such as IFN-γ fall within the group of LT-β-R activating agents of this invention. For example, interferons can be induced by treating with double-stranded RNA molecules such as polyriboguanylic/polyribocytidylic acid (poly-G/C).

Female C57/b16 (6–8 weeks old) can be injected with 18 mg (600 mg/kg) of D-galactosamine which sensitizes mice to the effects of TNF and other anti-tumor agents. A series of concentrations of poly-G/C (Juraskova et al., Eur. J. Pharmacol., 221, pp. 107–11 (1992)) in a neutral saline solution is added to purified LT-α1/β2 (10–100 µg) and the solution administered to mice as an intraperitoneal (i.p.) injection. The anti-tumor activity of LT-α1/β2 will be enhanced by the presence of poly-rG/rC double stranded RNA.

Similarly, the interferon stimulator from the plant Glycyrrhiza glabra (Acharya et al., Indian J. Med. Res., 98, pp. 69–74 (1993)) may be administered to humans intravenously at doses ranging from 40–100 ml/day. The optimal dose for LT-β-R activation in the presence of either LT-α/β heteromeric complexes or anti-LT-β-R Abs may be determined empirically and will depend on factors such as the tumor type, mode of delivery and delivery schedule.

Imiquimod R-837 (Bernstein et al., Antiviral Res., 20, pp. 45–55 (1994)); Saparal (Paramonova et al., Vopr. Virusol., 39, pp. 131–34 (1994)); Bropirimine (Onishi and Machida, Hinyokika Kiyo, 40, pp. 195–200 (1994)); or Ridostin (Cheknev et al., Vopr. Virusol., 39, pp. 125–28 (1994)), may also be administered as LT-β-R activating agents in conjunction with LT-α/β heteromeric complexes, anti-LT-β-R Abs, or a combination thereof. In each case, the preferred modes of delivery and optimal doses can be determined empirically using the published reports as starting points for optimization by routine clinical procedures.

EXAMPLE 11

Mice Tolerate Injections of Human LT-α1/β2

Female C57/b16 (6–8 weeks old) acclimated to the facility for several days were injected i.p. with 18 mg (600 mg/kg) of D-galactosamine, which sensitizes mice to the effects of TNF and other anti-tumor agents. Either human TNF, LT-α or LT-α1/β2 was then given i.p. Table 3 documents the survival of treated mice 24 hours after injection.

TABLE 3

| Agent | Dose (µg/animal) | Survival |
|---|---|---|
| saline | — | 4/4 |
| hu-TNF | 0.2 | 0/6 |
| hu-TNF | 1.0 | 0/2 |
| hu-TNF | 10 | 0/4 |
| hu-LT-α | 0.2 | 2/2 |
| hu-LT-α | 1.0 | 2/2 |
| hu-LT-α1/β2 | 10 | 2/2 |
| hu-LT-α1/β2 | 100 | 2/2 |

EXAMPLE 12

Construction of a Recombinant Anti-LT-β-R IgM Monoclonal Antibody

Using the anti-tumor cytotoxicity assays described above coupled with standard tumor growth models in immunodeficient mice, an anti-LT-β-R IgG with suitable properties can be selected. Universal primers which hybridize to each of the variable domains of the IgG heavy and light chains of the selected anti-LT-β-R IgG can be used to prepare variable domain DNA from RNA isolated from the secreting hybridoma cell line using standard reverse transcriptase/PCR methodologies. These protocols have been described (Arulanadam et al., *J. Exp. Med.*, 177, pp. 1439–50 (1993); Lane et al., *Eur. J. Immunol.*, 22, pp. 2573–78 (1993); Traunecker et al., *Nature*, 339, pp. 68–70 (1989)).

The amplified products are then assembled into vectors containing the human CH1, CH2 and CH3 µ chain domains. Co-expression of the two chains in a single host will allow assembly of the heavy and light chains into a pentameric IgM molecule. This molecule is a chimera composed of mouse variable regions coupled to human constant regions.

Alternatively, a process using PCR to amplify DNA encoding only the actual binding regions of the variable regions can be used. Amplified DNA is then inserted into vectors containing all of the human IgG sequences except for the actual amino acids involved in binding the antigen. Such constructs are called "humanized" antibodies and the detailed methods for their production are well-known (e.g. WO 94/04679).

EXAMPLE 13

Anti-LT-β-R IgM Monoclonal Antibodies Function as LT-β-R Activating Agents

Anti-LT-β-R IgM antibodies can be prepared in a recombinant form as described in Example 12. Alternatively, complete mouse IgMs isolated by hybridoma fusion techniques using primary immunization of normal mice or extensive immunization of CD40 signaling-deficient mice (Kawabe et al., *Immunity*, 1, pp. 167–78 (1994); Xu et al., *Immunity*, 1, pp. 423–31 (1994)) can be used as a source of anti-LT-β-R IgM mAbs.

Anti-LT-β-R IgM mAbs will be significantly more potent as LT-β-R activating agents than their normal bivalent IgG counterparts as measured by dose-response comparisons in the HT29 cytolytic assay in the presence of IFN-γ. The anti-LT-β-R IgM mAbs function as LT-β-R activating agents both when they are immobilized and when they are administered in solution. In addition, we expect that they will augment the anti-tumor activity of LT-α/β heteromeric complexes.

EXAMPLE 14

Anti-LT-β-R Monoclonal Antibodies Inhibit the Growth of Human Tumor Cells in SCID Mice Balb/c SCID mice (Jackson Labs, Bar Harbor, Me.) were injected with $1 \times 10^6$ trypsinized and washed human adenocarcinoma WiDr cells in a volume of 0.2 ml of PBS subcutaneously (s.c.) onto the back of the animal. Injected WiDr cells form tumors in the mice, and the ability of an anti-LT-β-R mAb to inhibit tumor growth was monitored. In one set of experiments, mice were treated with or without the CBE11 anti-LT-β-R mAb—either with or without human IFN-γ ($10^6$ antiviral units/mouse)—at the same time as the WiDr cells were inoculated s.c. (FIG. 6A). Antibodies and IFN-γ were administered alone or together by i.p. injection in 0.2 ml. Control mice were injected with saline alone, IFN-γ alone, or a control anti-human LFA-3 mAb (1E6) with IFN-γ. The size of each resulting tumor as scored 30 days after inoculation. Tumor volume (in cc) was calculated from the radius as determined by caliper measurements in two dimensions. Animals treated with CBE11 or 1E6 mAbs received 10 µg/mouse or 50 µg/mouse of antibody (FIG. 6A; circles with dots and open circles, respectively).

In another set of experiments, mice were inoculated s.c. with the WiDr cells and tumors were allowed to grow for 15 days before the mice were treated with the CBE11 anti-LT-β-R mAb (FIG. 6B). At day 15 (before antibody treatment), the average tumor volume was 0.076 cc with an average diameter of 0.53 cm. The CBE11 anti-LT-β-R mAb (50 µg) was then administered—either with or without human IFN-γ ($10^6$ antiviral units/mouse)—by i.p. injection in 0.2 ml to a group of 12 animals. Injections were repeated three or more times over a three week period. Control groups (12 mice/group) were injected with IFN-γ alone ($10^6$ antiviral units/mouse) or with 50 µg of a control anti-human LFA-3 mAb (1E6)+IFN-γ ($10^6$ antiviral units/mouse). The growth of the tumors present at day 15 was scored over time, from 15 to 49 days post-tumor cell inoculation. The results shown in FIG. 6B were determined in a blinded format. Tumors treated with CBE11 mAb either with or without IFN-γ stopped growing. Following three injections of CBE11 mAb (+/−IFN-γ) over three weeks, tumor growth was arrested for at least 7 weeks post-inoculum, at which time the experiment was terminated.

---

Applicant's or agent's file reference number: B185 CIP PCT International application No.

INDICATIONS RELATING TO A DEPOSITED MICROORGANISM
(PCT Rule 13bis)

A. The indications made below relate to the microorganism referred to in the description
on page 28, lines 18-26

-continued

Applicant's or agent's file reference number  B185 CIP PCT International application No.

INDICATIONS RELATING TO A DEPOSITED MICROORGANISM
(PCT Rule 13bis)

B. IDENTIFICATION OF DEPOSIT    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, CB.E11.1

Date of deposit      Accession Number
    12 January 1995 (12.01.95)      HB 11793

C. ADDITIONAL INDICATIONS (leave blank if not applicable) This information is continued on an additional sheet ☒

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only      For International Bureau use only
☐ This sheet was received with the international application ☐ This sheet was received by the International Bureau on:

A. The indications made below relate to the microorganism referred to in the description
    on page    28   , lines    18-26

B. IDENTIFICATION OF DEPOSIT    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BC.G6.AF5

Date of deposit      Accession Number
    12 January 1995 (12.01.95)      HB 11794

C. ADDITIONAL INDICATIONS (leave blank if not applicable) This information is continued on an additional sheet ☒

-continued

| Applicant's or agent's file reference number | B185 CIP PCT International application No. |
|---|---|

INDICATIONS RELATING TO A DEPOSITED MICROORGANISM
(PCT Rule 13bis)

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

E. SEPARATE FURNISHING OF INDICATIONS (leave blank if not applicable)

The indications listed below will be submitted to the International Bureau later (specify the general nature of the indications e.g., "Accession
Number of Deposit")

| For receiving Office use only | For International Bureau use only |
|---|---|
| ☐ This sheet was received with the international application | ☐ This sheet was received by the International Bureau on: |
| Authorized officer | Authorized officer |

A. The indications made below relate to the microorganism referred to in the description
on page ___28___, lines ___18-26___

B. IDENTIFICATION OF DEPOSIT                    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BH.A10

| Date of deposit | Accession Number |
|---|---|
| 12 January 1995 (12.01.95) | HB 11795 |

C. ADDITIONAL INDICATIONS (leave blank if not applicable) This information is continued on an additional sheet ☒

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

E. SEPARATE FURNISHING OF INDICATIONS (leave blank if not applicable)

-continued

Applicant's or agent's file reference number: B185 CIP PCT International application No.

INDICATIONS RELATING TO A DEPOSITED MICROORGANISM
(PCT Rule 13bis)

The indications listed below will be submitted to the International Bureau later (specify the general nature of the indications e.g., "Accession Number of Deposit")

For receiving Office use only  
☐ This sheet was received with the international application For International Bureau use only  
☐ This sheet was received by the International Bureau on:

Authorized officer

Authorized officer

A. The indications made below relate to the microorganism referred to in the description
on page ___28___, lines ___18-26___

B. IDENTIFICATION OF DEPOSIT  Further deposits are identified on an additional sheet ☒

Name of depositary institution
American Type Culture Collection

Address of depositary institution (including postal code and country)
12301 Parklawn Drive
Rockville, Maryland 20852
United States of America
Identification Reference by Depositor: Hybridoma, AG.H1.5.1

Date of deposit  Accession Number
12 January 1995 (12.01.95)  HB 11796

C. ADDITIONAL INDICATIONS (leave blank if not applicable) This information is continued on an additional sheet ☒

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only  
☐ This sheet was received with the international application For International Bureau use only  
☐ This sheet was received by the International Bureau on:

Authorized officer

Authorized officer

A. The indications made below relate to the microorganism referred to in the description
on page ___28___, lines ___18-26___

-continued

| Applicant's or agent's file reference number | B185 CIP PCT International application No. |

INDICATIONS RELATING TO A DEPOSITED MICROORGANISM
(PCT Rule 13bis)

B. IDENTIFICATION OF DEPOSIT                    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, CD.H10.1

Date of deposit          Accession Number
    12 January 1995 (12.01.95)    HB 11797

C. ADDITIONAL INDICATIONS (leave blank if not applicable) This information is continued on an additional sheet ☒

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only          For International Bureau use only
☐ This sheet was received with the international application ☐ This sheet was received by the International Bureau on:

Authorized officer          Authorized officer

A. The indications made below relate to the microorganism referred to in the description
    on page   28   , lines   18-26

B. IDENTIFICATION OF DEPOSIT                    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BD.A8.AB9

Date of deposit          Accession Number
    12 January 1995 (12.01.95)    HB 11798

-continued

| Applicant's or agent's file reference number | B185 CIP PCT International application No. |
|---|---|

INDICATIONS RELATING TO A DEPOSITED MICROORGANISM
(PCT Rule 13bis)

C. ADDITIONAL INDICATIONS (leave blank if not applicable) This information is continued on an additional sheet ☒

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

E. SEPARATE FURNISHING OF INDICATIONS (leave blank if not applicable)

The indications listed below will be submitted to the International Bureau later (specify the general nature of the indications e.g., "Accession
Number of Deposit")

| For receiving Office use only | For International Bureau use only |
|---|---|
| ☐ This sheet was received with the international application | ☐ This sheet was received by the International Bureau on: |
| Authorized officer | Authorized officer |

A. The indications made below relate to the microorganism referred to in the description
on page ___28___, lines ___18-26___

B. IDENTIFICATION OF DEPOSIT          Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BK.A11.AC10

| Date of deposit | Accession Number |
|---|---|
| 12 January 1995 (12.01.95) | HB 11799 |

C. ADDITIONAL INDICATIONS (leave blank if not applicable) This information is continued on an additional sheet ☒

In respect of the designation of the EPO, samples of the deposited microorganisms will be made available until the publication of the mention of the grant of the European patent or until the date on which the application is refused or withdrawn or is deemed to be withdrawn, as provided in Rule 28(3) of the Implementing Regulations under the EPC only by the issue of a sample to an expert nominated by requester (Rule 20(4) EPC).

D. DESIGNATED STATES FOR WHICH INDICATIONS ARE MADE (if the indications are not for all designated States)

EPO

-continued

| Applicant's or agent's file reference number | B185 CIP PCT International application No. |

INDICATIONS RELATING TO A DEPOSITED MICROORGANISM
(PCT Rule 13bis)

---

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only  For International Bureau use only
☐ This sheet was received with the international application ☐ This sheet was received by the International Bureau on:

Authorized officer  Authorized officer

---

A. The indications made below relate to the microorganism referred to in the description
on page   28  , lines   18-26

---

B. IDENTIFICATION OF DEPOSIT  Further deposits are identified on an additional sheet ☒

Name of depositary institution
American Type Culture Collection

Address of depositary institution (including postal code and country)
12301 Parklawn Drive
Rockville, Maryland 20852
United States of America
Identification Reference by Depositor: Hybridoma, CB.E11.1

Date of deposit  Accession Number
12 January 1995 (12.01.95)  HB 11793

---

C. ADDITIONAL INDICATIONS (leave blank if not applicable) This information is continued on an additional sheet ☒

In respect of the designation of Finland, until the
application has been laid open to public inspection by the
Finnish Patent Office, or has been finally decided upon by
the Finnish Patent Office without having been laid open to
public inspection, samples of the deposited microorganisms
will be made available only to an expert in the art.

---

D. DESIGNATED STATES FOR WHICH INDICATIONS ARE MADE (if the indications are not for all designated States)

Finland

---

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only  For International Bureau use only
☐ This sheet was received with the international application ☐ This sheet was received by the International Bureau on:

Authorized officer  Authorized officer

---

A. The indications made below relate to the microorganism referred to in the description
on page   28  , lines   18-26

-continued

| Applicant's or agent's file reference number | B185 CIP PCT International application No. |

INDICATIONS RELATING TO A DEPOSITED MICROORGANISM
(PCT Rule 13bis)

---

B. IDENTIFICATION OF DEPOSIT                    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BC.G6.AF5

Date of deposit      Accession Number
    12 January 1995 (12.01.95)      HB 11794

C. ADDITIONAL INDICATIONS (leave blank if not applicable) This information is continued on an additional sheet ☒

In respect of the designation of Finland, until the application has been laid open to public inspection by the Finnish Patent Office, or has been finally decided upon by the Finnish Patent Office without having been laid open to public inspection, samples of the deposited microorganisms will be made available only to an expert in the art.

D. DESIGNATED STATES FOR WHICH INDICATIONS ARE MADE (if the indications are not for all designated States)

Finland

E. SEPARATE FURNISHING OF INDICATIONS (leave blank if not applicable)

The indications listed below will be submitted to the International Bureau later (specify the general nature of the indications e.g., "Accession Number of Deposit")

| For receiving Office use only | For International Bureau use only |
|---|---|
| ☐ This sheet was received with the international application | ☐ This sheet was received by the International Bureau on: |

Authorized officer          Authorized officer

A. The indications made below relate to the microorganism referred to in the description
    on page    28   , lines    18-26

B. IDENTIFICATION OF DEPOSIT                    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BH.A10

Date of deposit      Accession Number
    12 January 1995 (12.01.95)      HB 11795

-continued

| Applicant's or agent's file reference number | B185 CIP PCT International application No. |

INDICATIONS RELATING TO A DEPOSITED MICROORGANISM
(PCT Rule 13bis)

C. ADDITIONAL INDICATIONS (leave blank if not applicable) This information is continued on an additional sheet ☒

In respect of the designation of Finland, until the application has been laid open to public inspection by the Finnish Patent Office, or has been finally decided upon by the Finnish Patent Office without having been laid open to public inspection, samples of the deposited microorganisms will be made available only to an expert in the art.

D. DESIGNATED STATES FOR WHICH INDICATIONS ARE MADE (if the indications are not for all designated States)

Finland

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only    For International Bureau use only
☐ This sheet was received with the international application  ☐ This sheet was received by the International Bureau on:

Authorized officer    Authorized officer

A. The indications made below relate to the microorganism referred to in the description
   on page     28    , lines    18-26

B. IDENTIFICATION OF DEPOSIT    Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, AG.H1.5.1

Date of deposit              Accession Number
    12 January 1995 (12.01.95)      HB 11796

C. ADDITIONAL INDICATIONS (leave blank if not applicable) This information is continued on an additional sheet ☒

In respect of the designation of Finland, until the application has been laid open to public inspection by the Finnish Patent Office, or has been finally decided upon by the Finnish Patent Office without having been laid open to public inspection, samples of the deposited microorganisms will be made available only to an expert in the art.

D. DESIGNATED STATES FOR WHICH INDICATIONS ARE MADE (if the indications are not for all designated States)

Finland

E. SEPARATE FURNISHING OF INDICATIONS (leave blank if not applicable)

-continued

| | |
|---|---|
| Applicant's or agent's file reference number | B185 CIP PCT International application No. |

INDICATIONS RELATING TO A DEPOSITED MICROORGANISM
(PCT Rule 13bis)

The indications listed below will be submitted to the International Bureau later (specify the general nature of the indications e.g., "Accession Number of Deposit")

For receiving Office use only        For International Bureau use only
☐ This sheet was received with the international application ☐ This sheet was received by the International Bureau on:

Authorized officer        Authorized officer

A. The indications made below relate to the microorganism referred to in the description
    on page   28  , lines   18-26

B. IDENTIFICATION OF DEPOSIT        Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, CD.H10.1

Date of deposit        Accession Number
    12 January 1995 (12.01.95)      HB 11797

C. ADDITIONAL INDICATIONS (leave blank if not applicable) This information is continued on an additional sheet ☒

In respect of the designation of Finland, until the
    application has been laid open to public inspection by the
    Finnish Patent Office, or has been finally decided upon by
    the Finnish Patent Office without having been laid open to
    public inspection, samples of the deposited microorganisms
    will be made available only to an expert in the art.

D. DESIGNATED STATES FOR WHICH INDICATIONS ARE MADE (if the indications are not for all designated States)

Finland

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only        For International Bureau use only
☐ This sheet was received with the international application ☐ This sheet was received by the International Bureau on:

Authorized officer        Authorized officer

A. The indications made below relate to the microorganism referred to in the description
    on page   28  , lines   18-26

B. IDENTIFICATION OF DEPOSIT        Further deposits are identified on an additional sheet ☒

-continued

| | |
|---|---|
| Applicant's or agent's file reference number | B185 CIP PCT International application No. |

INDICATIONS RELATING TO A DEPOSITED MICROORGANISM
(PCT Rule 13bis)

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BD.A8.AB9

| Date of deposit | Accession Number |
|---|---|
| 12 January 1995 (12.01.95) | HB 11798 |

C.   ADDITIONAL INDICATIONS (leave blank if not applicable) This information is continued on an additional sheet ☒

In respect of the designation of Finland, until the
    application has been laid open to public inspection by the
    Finnish Patent Office, or has been finally decided upon by
    the Finnish Patent Office without having been laid open to
    public inspection, samples of the deposited microorganisms
    will be made available only to an expert in the art.

D.   DESIGNATED STATES FOR WHICH INDICATIONS ARE MADE (if the indications are not for all designated States)

Finland

E.   SEPARATE FURNISHING OF INDICATIONS (leave blank if not applicable)

The indications listed below will be submitted to the International Bureau later (specify the general nature of the indications e.g., "Accession
Number of Deposit")

| For receiving Office use only | For International Bureau use only |
|---|---|
| ☐ This sheet was received with the international application | ☐ This sheet was received by the International Bureau on: |
| Authorized officer | Authorized officer |

A.   The indications made below relate to the microorganism referred to in the description
    on page    28   , lines    18-26

B.   IDENTIFICATION OF DEPOSIT             Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BK.A11.AC10

| Date of deposit | Accession Number |
|---|---|
| 12 January 1995 (12.01.95) | HB 11799 |

C.   ADDITIONAL INDICATIONS (leave blank if not applicable) This information is continued on an additional sheet ☒

-continued

| Applicant's or agent's file reference number | B185 CIP PCT International application No. |

INDICATIONS RELATING TO A DEPOSITED MICROORGANISM
(PCT Rule 13bis)

In respect of the designation of Finland, until the application has been laid open to public inspection by the Finnish Patent Office, or has been finally decided upon by the Finnish Patent Office without having been laid open to public inspection, samples of the deposited microorganisms will be made available only to an expert in the art.

D. DESIGNATED STATES FOR WHICH INDICATIONS ARE MADE (if the indications are not for all designated States)

Finland

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only                        For International Bureau use only
☐ This sheet was received with the international application  ☐ This sheet was received by the International Bureau on:

Authorized officer                                   Authorized officer

A. The indications made below relate to the microorganism referred to in the description
   on page ___28___, lines ___18-26___

B. IDENTIFICATION OF DEPOSIT                         Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, CB.E11.1

Date of deposit              Accession Number
    12 January 1995 (12.01.95)    HB 11793

C. ADDITIONAL INDICATIONS (leave blank if not applicable) This information is continued on an additional sheet ☒

Applicant(s) hereby give notice of my/our intention that
samples of the above-identified culture shall be available
only to experts in accordance with paragraph 3 of the
Fourth Schedule to the Patents Rules 1995.

D. DESIGNATED STATES FOR WHICH INDICATIONS ARE MADE (if the indications are not for all designated States)

Singapore

E. SEPARATE FURNISHING OF INDICATIONS (leave blank if not applicable)

The indications listed below will be submitted to the International Bureau later (specify the general nature of the indications e.g., "Accession
Number of Deposit")

-continued

| | |
|---|---|
| Applicant's or agent's file reference number | B185 CIP PCT International application No. |

INDICATIONS RELATING TO A DEPOSITED MICROORGANISM
(PCT Rule 13bis)

For receiving Office use only      For International Bureau use only
☐ This sheet was received with the international application    ☐ This sheet was received by the International Bureau on:

Authorized officer                   Authorized officer

A. The indications made below relate to the microorganism referred to in the description
    on page   28  , lines   18-26

B. IDENTIFICATION OF DEPOSIT          Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BC.G6.AF5

Date of deposit          Accession Number
    12 January 1995 (12.01.95)      HB 11794

C. ADDITIONAL INDICATIONS (leave blank if not applicable) This information is continued on an additional sheet ☒

Applicant(s) hereby give notice of my/our intention that
    samples of the above-identified culture shall be available
    only to experts in accordance with paragraph 3 of the
    Fourth Schedule to the Patents Rules 1995.

D. DESIGNATED STATES FOR WHICH INDICATIONS ARE MADE (if the indications are not for all designated States)

Singapore

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only      For International Bureau use only
☐ This sheet was received with the international application    ☐ This sheet was received by the International Bureau on:

Authorized officer                   Authorized officer

A. The indications made below relate to the microorganism referred to in the description
    on page   28  , lines   18-26

B. IDENTIFICATION OF DEPOSIT          Further deposits are identified on an additional sheet ☒

Name of depositary institution
    American Type Culture Collection

-continued

| Applicant's or agent's file reference number | B185 CIP PCT International application No. |

INDICATIONS RELATING TO A DEPOSITED MICROORGANISM
(PCT Rule 13bis)

Address of depositary institution (including postal code and country)
    12301 Parklawn Drive
    Rockville, Maryland 20852
    United States of America
Identification Reference by Depositor: Hybridoma, BH.A10

Date of deposit            Accession Number
    12 January 1995 (12.01.95)     HB 11795

C. ADDITIONAL INDICATIONS (leave blank if not applicable) This information is continued on an additional sheet ☒

Applicant(s) hereby give notice of my/our intention that
    samples of the above-identified culture shall be available
    only to experts in accordance with paragraph 3 of the
    Fourth Schedule to the Patents Rules 1995.

D. DESIGNATED STATES FOR WHICH INDICATIONS ARE MADE (if the indications are not for all designated States)

Singapore

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only                 For International Bureau use only
☐ This sheet was received with the international application ☐ This sheet was received by the International Bureau on:

Authorized officer                 Authorized officer

A. The indications made below relate to the microorganism referred to in the description
    on page    28   , lines   18-26

B. IDENTIFICATION OF DEPOSIT                 Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, AG.H1.5.1

Date of deposit            Accession Number
    12 January 1995 (12.01.95)     HB 11796

C. ADDITIONAL INDICATIONS (leave blank if not applicable) This information is continued on an additional sheet ☒

Applicant(s) hereby give notice of my/our intention that
    samples of the above-identified culture shall be available
    only to experts in accordance with paragraph 3 of the
    Fourth Schedule to the Patents Rules 1995.

D. DESIGNATED STATES FOR WHICH INDICATIONS ARE MADE (if the indications are not for all designated States)

-continued

Applicant's or agent's file reference number: B185 CIP PCT International application No.

INDICATIONS RELATING TO A DEPOSITED MICROORGANISM
(PCT Rule 13bis)

Singapore

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only     For International Bureau use only
☐ This sheet was received with the international application ☐ This sheet was received by the International Bureau on:

Authorized officer     Authorized officer

A. The indications made below relate to the microorganism referred to in the description
on page ___28___, lines ___18-26___

B. IDENTIFICATION OF DEPOSIT     Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, CD.H10.1

Date of deposit     Accession Number
    12 January 1995 (12.01.95)     HB 11797

C. ADDITIONAL INDICATIONS (leave blank if not applicable) This information is continued on an additional sheet ☒

Applicant(s) hereby give notice of my/our intention that
samples of the above-identified culture shall be available
only to experts in accordance with paragraph 3 of the
Fourth Schedule to the Patents Rules 1995.

D. DESIGNATED STATES FOR WHICH INDICATIONS ARE MADE (if the indications are not for all designated States)

Singapore

E. SEPARATE FURNISHING OF INDICATIONS (leave blank if not applicable)

The indications listed below will be submitted to the International Bureau later (specify the general nature of the indications e.g., "Accession Number of Deposit")

For receiving Office use only     For International Bureau use only
☐ This sheet was received with the international application ☐ This sheet was received by the International Bureau on:

Authorized officer     Authorized officer

A. The indications made below relate to the microorganism referred to in the description -continued

| Applicant's or agent's file reference number | B185 CIP PCT International application No. |

INDICATIONS RELATING TO A DEPOSITED MICROORGANISM
(PCT Rule 13bis)

on page ___28___, lines ___18-26___

B.  IDENTIFICATION OF DEPOSIT                         Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BD.A8.AB9

Date of deposit      Accession Number
    12 January 1995 (12.01.95)     HB 11798

C.  ADDITIONAL INDICATIONS (leave blank if not applicable) This information is continued on an additional sheet ☒

Applicant(s) hereby give notice of my/our intention that
samples of the above-identified culture shall be available
only to experts in accordance with paragraph 3 of the
Fourth Schedule to the Patents Rules 1995.

D.  DESIGNATED STATES FOR WHICH INDICATIONS ARE MADE (if the indications are not for all designated States)

Singapore

E.  SEPARATE FURNISHING OF INDICATIONS (leave blank if not applicable)

The indications listed below will be submitted to the International Bureau later (specify the general nature of the indications e.g., "Accession
Number of Deposit")

| For receiving Office use only | For International Bureau use only |
| ☐ This sheet was received with the international application | ☐ This sheet was received by the International Bureau on: |

Authorized officer                   Authorized officer

A.  The indications made below relate to the microorganism referred to in the description
    on page ___28___, lines ___18-26___

B.  IDENTIFICATION OF DEPOSIT                         Further deposits are identified on an additional sheet ☒

Name of depositary institution
    American Type Culture Collection

Address of depositary institution (including postal code and country)
    12301 Parklawn Drive
    Rockville, Maryland 20852
    United States of America
Identification Reference by Depositor: Hybridoma, BK.A11.AC10

Date of deposit      Accession Number
    12 January 1995 (12.01.95)     HB 11799

-continued

| Applicant's or agent's file reference number | B185 CIP PCT International application No. |

INDICATIONS RELATING TO A DEPOSITED MICROORGANISM
(PCT Rule 13bis)

C. ADDITIONAL INDICATIONS (leave blank if not applicable) This information is continued on an additional sheet ☒

Applicant(s) hereby give notice of my/our intention that samples of the above-identified culture shall be available only to experts in accordance with paragraph 3 of the Fourth Schedule to the Patents Rules 1995.

D. DESIGNATED STATES FOR WHICH INDICATIONS ARE MADE (if the indications are not for all designated States)

Singapore

E. SEPARATE FURNISHING OF INDICATIONS (leave blank if not applicable)

The indications listed below will be submitted to the International Bureau later (specify the general nature of the indications e.g., "Accession
Number of Deposit")

For receiving Office use only          For International Bureau use only
☐ This sheet was received with the international application  ☐ This sheet was received by the International Bureau on:

Authorized officer          Authorized officer

What is claimed is:

1. A method for treating or reducing the advancement, severity or effects of neoplasia comprising the step of administering a therapeutically effective amount of at least one LT-β-R activating agent and a pharmaceutically acceptable carrier wherein at least one LT-β-R activating agent comprises an anti-LT-β-R antibody.

2. The method according to claim 1, wherein the anti-LT-β-R antibody is CBE11 (ATCC Accession No. 11793).

3. A pharmaceutical composition comprising a therapeutically effective amount of at least one anti-LT-β-R activating agent wherein one anti-LT-β-R activating agent is an anti-LT-β-R antibody.

4. The pharmaceutical composition according to claim 3, wherein the anti-LT-β-R antibody is a monoclonal antibody.

5. The pharmaceutical composition according to claim 4, wherein the anti-LT-β-R monoclonal antibody is selected from the group consisting of anti-LT-β-R mAb CBE11 (ATCC Accession No. 11793), BKA11 (ATCC Accession No. 11799), CDH10 (ATCC Accession No. 11797), BCG6 (ATCC Accession No. 11794), and BHA10 (ATCC Accession No. 11795).

* * * * *

UNITED STATES PATENT AND TRADEMARK OFFICE
CERTIFICATE OF CORRECTION

PATENT NO. : 6,312,691 B1
DATED : November 6, 2001
INVENTOR(S) : Jeffrey L. Browning, Werner Meier and Christopher D. Benjamin It is certified that error appears in the above-identified patent and that said Letters Patent is hereby corrected as shown below:

Title page,
Item [54], "LYMPHOTOXIN-α/β COMPLEXES AND ANTI-LYMPOTOXIN-β RECEPTOR ANTIBODIES AS ANTI-TUMOR AGENTS" should read,
-- LYMPHOTOXIN-α/β COMPLEXES AND ANTI-LYMPHOTOXIN-β RECEPTOR ANTIBODIES AS ANTI-TUMOR AGENTS --

Item [56], under "OTHER PUBLICATIONS"
Browning, Jeffrey and Ngam-ek, Apinya et al. citation: "TNGF" should be -- TNF --.
Crowne, Paul, VanArsdale, Todd et al. ..."Production of lymphotoxin..." citation: "Crowne, Paul, VanArsdale," should be -- Crowe, Paul, VanArsdale --.
Crowne, Paul, VanArsdale, Todd et al. ..."A Lymphotoxin Beta...." citation: "Crowne, Paul, VanArsdale," should be -- Crowe, Paul, VanArsdale --.
Dighe, Anand et al. citation: "Rejectionof" should be -- Rejection of --.
Dighe, Anand et al. citation: "IFNy" should be -- IFNγ --.
Eppstein, Deborah citation: "interferon y" should be -- interferon γ --.
Fukushima, Keiko et al. citation: "Clearacne" should be -- Clearance --.
Havell, Edward et al. citation: "Anittumor" should be -- Antitumor --.
Kopp, William C. et al. citation: "Inteferon—y" should be -- Interferon—γ --.
Loetshcer, Hansruedi et al. citation: "(TNGF)" should be -- (TGF) --.
Niederle, Norbert et al. citation: "...Tretment..." should be -- Treatment --.
Pleskov, V.M. et al. citation: "...Viruese..." should be -- Virus --.
Raitano, Arthur B. et al. citation: "y—Interferon" should be -- γ—Interferon --.
Schoenfeld, Hans-Joachim et al. citation: "Purificationof" should be -- Purification of --.
Schoenfeld, Hans-Joachim et al. citation: "Facotr" should be -- Factor --.
Stepushkin, A.N. et al. citation: "Reactogenicty" should be -- Reactogenicity --.
Traunecker, Andre et al. citation: "neutralizationof" should be -- neutralization of --.

Column 1,
Line 2, "ANTI-LYMPOTOXIN-β" should be -- ANTI-LYMPHOTOXIN-β --.

Column 2,
Line 23, "severity of" should read -- severity or --.
Line 40, "a LT-β-R" should read -- an LT-β-R --.
Line 66, after "Abs used", insert -- in --.

UNITED STATES PATENT AND TRADEMARK OFFICE
CERTIFICATE OF CORRECTION

PATENT NO.    : 6,312,691 B1
DATED         : November 6, 2001
INVENTOR(S)   : Jeffrey L. Browning, Werner Meier and Christopher D. Benjamin It is certified that error appears in the above-identified patent and that said Letters Patent is hereby corrected as shown below:

Column 3,
Line 7, "anti-β-R" should read -- anti-LT-β-R --.

Column 4,
Line 56, "50 g" should read -- 50 μg --.

Column 6,
Line 63, "with" should read -- which --.

Column 8,
Line 32, "form" should read -- from --.
Line 66, "Crow" should read -- Crowe --.

Signed and Sealed this

Sixteenth Day of July, 2002

Attest:

Attesting Officer

JAMES E. ROGAN
Director of the United States Patent and Trademark Office